United States Patent
Mutz et al.

(10) Patent No.: US 6,808,934 B2
(45) Date of Patent: Oct. 26, 2004

(54) HIGH-THROUGHPUT BIOMOLECULAR CRYSTALLIZATION AND BIOMOLECULAR CRYSTAL SCREENING

(75) Inventors: Mitchell W. Mutz, Palo Alto, CA (US); Richard N. Ellson, Palo Alto, CA (US); Richard G. Stearns, Felton, CA (US)

(73) Assignee: Picoliter Inc., Mountain View, CA (US)

( * ) Notice: Subject to any disclaimer, the term of this patent is extended or adjusted under 35 U.S.C. 154(b) by 293 days.

(21) Appl. No.: 10/055,245

(22) Filed: Jan. 22, 2002

(65) Prior Publication Data

US 2002/0191048 A1 Dec. 19, 2002

Related U.S. Application Data

(63) Continuation-in-part of application No. 09/765,947, filed on Jan. 19, 2001, now abandoned, which is a continuation-in-part of application No. 09/727,392, filed on Nov. 29, 2000, now abandoned, which is a continuation-in-part of application No. 09/669,996, filed on Sep. 25, 2000, now abandoned.

(51) Int. Cl.[7] .................................................. G01N 1/10
(52) U.S. Cl. .................... 436/180; 436/86; 436/174; 436/166; 436/73; 436/1.83
(58) Field of Search .......................... 436/86, 174, 180, 436/164, 166; 73/1.83

(56) References Cited

U.S. PATENT DOCUMENTS

| | | | |
|---|---|---|---|
| 4,308,547 A | 12/1981 | Lovelady et al. | |
| 4,697,195 A | 9/1987 | Quate et al. | |
| 4,719,476 A | 1/1988 | Elrod et al. | |
| 4,751,529 A | 6/1988 | Elrod et al. | |
| 4,751,530 A | 6/1988 | Elrod et al. | |
| 4,751,534 A | 6/1988 | Elrod et al. | |
| 4,797,693 A | 1/1989 | Quate | |
| 4,801,953 A | 1/1989 | Quate | |
| 4,959,674 A | 9/1990 | Khri-Yakub et al. | |
| 5,041,849 A | 8/1991 | Quate et al. | |
| 5,087,931 A | 2/1992 | Rawson | |
| 5,122,818 A | 6/1992 | Elrod et al. | |

(List continued on next page.)

FOREIGN PATENT DOCUMENTS

| EP | 0913507 A1 | 5/1999 |
|---|---|---|
| WO | WO 90/15070 | 12/1990 |
| WO | WO 00/78445 A1 | 12/2000 |

OTHER PUBLICATIONS

Hey et al. "A new device for multifunctional dosage of liquids by a free jet", Proceedings—IEEE Annual International Workshop on Micro Electro Mechanical Systems, 11th, Heidelberg, Jan. 25–29, 1998, 429–431, Abstract.*

(List continued on next page.)

*Primary Examiner*—Yelena G. Gakh
(74) *Attorney, Agent, or Firm*—Dianne E. Reed; Reed & Eberle LLP

(57) ABSTRACT

The present invention provides a method for the acoustic ejection of fluid droplets from fluid-containing reservoirs to form arrays suitable for high-throughput combinatorial crystallization experiments. Such arrays may utilize very small fluid volumes, in the order of picoliters. The method is especially suited to preparing combinatorial libraries useful in developing techniques for crystallizing biomacromolecules, such as proteins. The small volumes conserve macromolecules that may be costly and rare, and permit the testing of a large number of experimental crystallization conditions for a given amount of a macromolecule. The time required for the experiments may be very short due to the small volumes. The invention is conducive to forming high-density microarrays of small volume crystallization experiments. Acoustic detection of crystals in situ, and distinction between biomacromolecular and non-biomacromolecular crystals, are also taught.

87 Claims, 7 Drawing Sheets

U.S. PATENT DOCUMENTS

| | | | |
|---|---|---|---|
| 5,143,854 | A | 9/1992 | Pirrung et al. |
| 5,216,451 | A | 6/1993 | Rawson et al. |
| 5,229,016 | A | 7/1993 | Hayes et al. |
| 5,229,793 | A | 7/1993 | Hadimioglu et al. |
| 5,231,426 | A | 7/1993 | Sweet |
| 5,339,101 | A | 8/1994 | Rawson et al. |
| 5,377,902 | A | 1/1995 | Hayes |
| 5,392,064 | A | 2/1995 | Hadimioglu et al. |
| 5,405,783 | A | 4/1995 | Pirrung et al. |
| 5,415,679 | A | 5/1995 | Wallace |
| 5,436,327 | A | 7/1995 | Southern et al. |
| 5,445,934 | A | 8/1995 | Fodor et al. |
| 5,498,444 | A | 3/1996 | Hayes |
| 5,520,715 | A | 5/1996 | Oeftering |
| 5,556,752 | A | 9/1996 | Lockhart et al. |
| 5,565,113 | A * | 10/1996 | Hadimioglu et al. .......... 216/2 |
| 5,591,490 | A | 1/1997 | Quate |
| 5,608,433 | A | 3/1997 | Quate |
| 5,629,724 | A | 5/1997 | Elrod et al. |
| 5,631,678 | A | 5/1997 | Hadimioglu et al. |
| 5,643,353 | A | 7/1997 | Wallace et al. |
| 5,658,802 | A | 8/1997 | Hayes et al. |
| 5,669,971 | A | 9/1997 | Bok et al. |
| 5,700,637 | A | 12/1997 | Southern |
| 5,722,479 | A | 3/1998 | Oeftering |
| 5,744,305 | A | 4/1998 | Fodor et al. |
| 5,798,779 | A | 8/1998 | Nakayasu et al. |
| 5,808,636 | A | 9/1998 | Stearns |
| 5,959,297 | A | 9/1999 | Weinberg et al. |
| 5,985,356 | A | 11/1999 | Schultz et al. |
| 6,004,617 | A | 12/1999 | Schultz et al. |
| 6,007,183 | A | 12/1999 | Horine |
| 6,010,316 | A | 1/2000 | Haller et al. |
| 6,015,880 | A | 1/2000 | Baldeschwieler et al. |
| 6,028,189 | A | 2/2000 | Blanchard |
| 6,029,896 | A | 2/2000 | Self et al. |
| 6,030,917 | A | 2/2000 | Weinberg et al. |
| 6,034,775 | A | 3/2000 | McFarland et al. |
| 6,045,671 | A | 4/2000 | Wu et al. |
| 6,054,270 | A | 4/2000 | Southern |
| 6,087,181 | A | 7/2000 | Cong |
| 6,187,164 | B1 | 2/2001 | Warren et al. |
| 6,296,673 | B1 * | 10/2001 | Santarsiero et al. ...... 23/295 R |
| 2002/0037359 | A1 | 3/2002 | Mutz et al. |
| 2002/0037579 | A1 | 3/2002 | Ellson et al. |
| 2002/0061258 | A1 | 5/2002 | Mutz et al. |

OTHER PUBLICATIONS

Subramanian et al. "Controlled Two–Step Solid–Phase Crystallization for High–Performance Polysilicon TFT's", IEEE Electron Device Letters, 1997, v. 18, No. 8, pp. 378–381.*

Lube et al. "In–process monitoring of crystal perfection during melt growth", Journal of Crystal Growth (1989), 98(4), 817–26, Abstract.*

U.S. patent application Ser. No. 09/727,392, Mutz et al., filed Nov. 29, 2000.

Allegra et al. (1972), "Attenuation of Sound in Suspensions and Emulsions: Theory and Experiments," *The Journal of the Acoustical Society of America* 51(5):1545–1564.

Calzolai et al. (2000), "NMR Structures of Three Single–Residue Variants of the Human Prion Protein," *Proc. Natl. Acad. Sci. USA* 97(15):8340–8345.

Chayen et al. (1990), "An Automated System for Micro-Batch Protein Crystallization and Screening," *J. Appl. Cryst.* 23:297–302.

Chayen (1997), "A Novel Technique to Control the Rate of Vapour Diffusion, Giving Larger Protein Crystals," *J. Appl. Cryst.* 30:198–202.

Creighton (1993), *Proteins*, $2^{nd}$ Edition, W.H. Freeman, pp. 171–260.

D'Arcy et al. (1996), "A Novel Approach to Crystallising Proteins Under Oil," *Journal of Crystal Growth* 168:175–180.

Elrod et al. (1989), "Nozzleless Droplet Formation with Focused Acoustic Beams," *J. Appl. Phys.* 65(9):3441–3447.

Hadimioglu et al. (1992), "Acoustic Ink Printing," *Ultrasonics Symposium*, pp. 929–935.

Jackson et al. (1999), "Multiple Folding Pathways for Heterologously Expressed Human Prion Protein," *Biochimica et Biophysica Acta* 1431:1–13.

Jordan et al. (1985), "Systematic Variation in DNA Length Yields Highly Ordered Repressor–Operator Cocrystals," *Science* 230:1383–1385.

Kendrew et al. (1956), "The Crystal Structure of Myoglobin III. Sperm–Whale Myoglobin," *Proc. R. Soc. Lond. A* 238:305–324.

Klug et al. (1995), "Zinc Fingers" *The FASEB Journal* 9:597–604.

Lorber et al. (1996), "Containerless Protein Crystallization in Floating Drops: Application to Crystal Growth Monitoring Under Reduced Nucleation Conditions," *Journal of Crystal Growth* 168:204–215.

MacBeath et al. (2000), "Printing Proteins as Microarrays for High–Throughput Function Determination," *Science* 289:1760–1763.

McRee (1999), *Practical Protein Crystallography*, $2^{nd}$ Edition, Academic Press, pp. 1–17 and 145–161.

Michel et al. (1980), "Three–Dimensional Crystals of Membrane Proteins: Bacteriorhodopsin," *Proc. Natl. Acad. Sci. USA* 77(3):1283–1285.

Moates et al. (1996), "Infrared Thermographic Screening of Combinatorial Libraries of Heterogeneous Catalysts," *Ind. Eng. Chem. Res.* 35:4801–4803.

Stevens (2000), "High–Throughput Protein Crystallization," *Curr. Opin. Struct. Biol.* 10:558–563.

Stura et al. (1994), "Reverse Screening," *Acta Crystallogr.* D50:448–455.

Theriault et al. (1999), "Application of Ink–jet Printing Technology to the Manufacture of Molecular Arrays," *DNA Microarrays, A Practical Approach*, Ed. M. Schena, Chapter 6 (Oxford University Press).

Zahn et al. (2000), "NMR Solution Structure of the Human Prion Protein," *Proc. Natl. Acad. Sci. USA* 97(1):145–150.

U.S. patent application Ser. No. 09/669,194, Ellson et al., filed Sep. 25, 2000.

U.S. patent application Ser. No. 09/669,267, Ellson, filed Sep. 25, 2000.

U.S. patent application Ser. No. 09/669,996, Ellson et al., filed Sep. 25, 2000.

U.S. patent application Ser. No. 09/669,997, Mutz et al., filed Sep. 25, 2000.

Amemiya et al. (1997), *Proceedings of the 1997 IS&T's NIP 13: 1997 International Conference on Digital Printing Technologies*, pp. 698–702.

IUPAC–IUB Commission on Biochemical Nomenclature (CBN) (1970), "Abbreviations and Symbols for Nucleic Acids, Polynucleotides and Their Constituents," *Biochemistry* 9(20):4022–4025.

Steel et al. (2000), "The Flow–Thru Chip™: A Three–Dimensional Biochip Platform," *Microarray Biochip Technology*, Chapter 5, pp. 87–117, BioTechniques Books, Natick, MA.

* cited by examiner

HIGH-THROUGHPUT BIOMOLECULAR CRYSTALLIZATION AND BIOMOLECULAR CRYSTAL SCREENING

CROSS-REFERENCE TO RELATED APPLICATIONS

This is a continuation-in-part of U.S. patent application Ser. No. 09/765,947, filed Jan. 19, 2001 now abandoned, which was a continuation-in-part of U.S. patent application Ser. No. 09/727,392, filed Nov. 29, 2000 now abandoned, which was a continuation-in-part of U.S. patent application Ser. No. 09/669,996, filed Sep. 25, 2000 now abandoned.

TECHNICAL FIELD

This invention relates generally to the production of crystals, particularly protein crystals, that are suitable for x-ray crystallographic structure determination. More particularly, the invention relates to optimizing the production of such crystals through the making and use of combinatorial arrays, which are employed to rapidly screen compositions and conditions affecting crystallization. The invention more specifically relates to the use of focused acoustic energy to eject nanoliter and subnanoliter-sized fluid droplets of protein solutions, ligands, crystallization-promoting moieties, and the like in a patterned, systematic combinatorial manner. The invention additionally permits control of non-compositional crystallization parameters, including temperature. The small volumes employed conserve protein while speeding up crystallization by reducing diffusion times. Such small-volume crystallization experiments may be conveniently arrayed on a substrate as virtual wells comprising droplets, or the droplets may reside in conventional wells.

BACKGROUND

The discovery of novel materials having useful biological, chemical and/or physical properties often leads to emergence of useful products and technologies. Extensive research in recent years has focused on the development and implementation of new methods and systems for evaluating potentially useful chemical compounds. In the biomacromolecule arena, for example, much recent research has been devoted to potential methods for rapidly and accurately identifying the properties of various oligomers of specific monomer sequences, including ligand and receptor interactions, by screening combinatorial libraries of biopolymers including nucleotidic, peptidic and saccharidic polymers. The properties of such combinatorial products offer potential utility for a variety of applications. Biological and non-biological combinatorial libraries can potentially be employed as superconducting materials, dielectric materials, magnetic materials (including resonance probes), phosphorescent materials, fluorescent materials, radiolabeling materials, photolabile materials, thermolabile moieties, optical materials, thermoelectric materials, separatory materials (including microporous separatory materials, physicochemical separation materials, and substrate-binding capability), and the like.

For biological molecules, the complexity and variability of biological interactions and the physical interactions that determine, for example, protein conformation or structure other than primary structure, preclude predictability of biological, material, physical and/or chemical properties from theoretical considerations at this time. For non-biological materials, including bulk liquids and solids, despite much inquiry and vast advances in understanding, a theoretical framework permitting sufficiently accurate prediction de novo of composition, structure and synthetic preparation of novel materials is still lacking.

Consequently, the discovery of novel useful materials depends largely on the capacity to make and characterize new compositions of matter. Of the elements in the periodic table that can be used to make multi-elemental compounds, relatively few of the practically inexhaustible possible compounds have been made or characterized. A general need in the art consequently exists for a more systematic, efficient and economical method for synthesizing novel materials and screening them for useful properties. Further, a need exists for a flexible method to make compositions of matter of various material types and combinations of material types, including molecular materials, crystalline covalent and ionic materials, alloys, and combinations thereof such as crystalline ionic and alloy mixtures, or crystalline ionic and alloy layered materials.

The immune system is an example of systematic protein and nucleic acid macromolecular combinatorial chemistry that is performed in nature. Both the humoral and cell-mediated immune systems produce molecules having novel functions by generating vast libraries of molecules that are systematically screened for a desired property. For example, the humoral immune system is capable of determining which of $10^{12}$ B-lymphocyte clones that make different antibody molecules bind to a specific epitope or immunogenic locale, in order to find those clones that specifically bind various epitopes of an immunogen and stimulate their proliferation and maturation into plasma cells that make the antibodies. Because T cells, responsible for cell-mediated immunity, include regulatory classes of cells and killer T cells, and the regulatory T cell classes are also involved in controlling both the humoral and cellular response, more clones of T cells exist than of B cells, and must be screened and selected for appropriate immune response. Moreover, the embryological development of both T and B cells is a systematic and essentially combinatorial DNA splicing process for both heavy and light chains. See, e.g., *Therapeutic Immunology*, Eds. Austen et al. (Blackwell Science, Cambridge Mass., 1996).

Recently, the combinatorial prowess of the immune system has been harnessed to select for antibodies against small organic molecules such as haptens; some of these antibodies have been shown to have catalytic activity akin to enzymatic activity with the small organic molecules as substrate, termed "catalytic antibodies" (Hsieh et al. (1993) *Science* 260(5106):337–9). The proposed mechanism of catalytic antibodies is a distortion of the molecular conformation of the substrate towards the transition state for the reaction and additionally involves electrostatic stabilization. Synthesizing and screening large libraries of molecules has, not unexpectedly, also been employed for drug discovery. Proteins are known to form an induced fit for a bound molecule such as a substrate or ligand (Stryer, *Biochemistry*, $4^{th}$ Ed. (1999) W. H. Freeman & Co., New York), with the bound molecule fitting into the site much like a hand fits into a glove, requiring some basic structure for the glove that is then shaped into the bound structure with the help of a substrate or ligand.

Geysen et al. (1987) *J. Immun. Meth.* 102:259–274 have developed a combinatorial peptide synthesis in parallel on rods or pins involving functionalizing the ends of polymeric rods to potentiate covalent attachment of a first amino acid, and sequentially immersing the ends in solutions of individual amino acids. In addition to the Geysen et al. method, techniques have recently been introduced for synthesizing large arrays of different peptides and other polymers on solid surfaces. Arrays may be readily appreciated as additionally being efficient screening tools. Miniaturization of arrays saves synthetic reagents and conserves sample, a useful improvement in both biological and non-biological contexts. See, for example, U.S. Pat. Nos. 5,700,637 and 6,054,270 to Southern et al., which describe a method for chemically synthesizing a high density array of oligonucleotides of chosen monomeric unit length within discrete cells or regions of a support material, wherein the method employs an inkjet printer to deposit individual monomers on the support. So far, however, miniaturized arrays have been costly to make and contain significant amounts of undesired products at sites where a desired product is made. Thus, even in the biological arena, where a given sample might be unique and therefore priceless, use of high density biomacromolecule microarrays has met resistance by the academic community as being too costly, as yet insufficiently reliable compared to arrays made by lab personnel.

Arrays of thousands or even millions of different compositions of the elements may be formed by such methods. Various solid phase microelectronic fabrication derived polymer synthetic techniques have been termed "Very Large Scale Immobilized Polymer Synthesis," or "VLSIPS" technology. Such methods have been successful in screening potential peptide and oligonucleotide ligands for determining relative binding affinity of the ligand for receptors.

The solid phase parallel, spatially directed synthetic techniques currently used to prepare combinatorial biomolecule libraries require stepwise, or sequential, coupling of monomers. U.S. Pat. No. 5,143,854 to Pirrung et al. describes synthesis of polypeptide arrays, and U.S. Pat. No. 5,744,305 to Fodor et al. describes an analogous method of synthesizing oligo- and poly-nucleotides in situ on a substrate by covalently bonding photoremovable groups to the surface of the substrate. Selected substrate surface locales are exposed to light to activate them, by use of a mask. An amino acid or nucleotide monomer with a photoremovable group is then attached to the activated region. The steps of activation and attachment are repeated to make polynucleotides and polypeptides of desired length and sequence. Other synthetic techniques, exemplified by U.S. Pat. Nos. 5,700,637 and 6,054,270 to Southern et al., teach the use of inkjet printers, which are also substantially parallel synthesis because the synthetic pattern must be predefined prior to beginning to "print" the pattern. These solid phase synthesis techniques, which involve the sequential coupling of building blocks (e.g., amino acids) to form the compounds of interest, cannot readily be used to prepare many inorganic and organic compounds.

U.S. Pat. No. 5,985,356 to Schultz et al. teaches combinatorial chemistry techniques in the field of materials science, providing methods and a device for synthesis and use of an array of diverse materials in predefined regions of a substrate. An array of different materials on a substrate is prepared by delivering components of various compositions of matter to predefined substrate surface locales. This synthetic technique permits many classes of materials to be made by systematic combinatorial methods. Examples of the types of materials include, but are not limited to, inorganic materials, including ionic and covalent crystalline materials, intermetallic materials, metal alloys and composite materials including ceramics. Such materials can be screened for useful bulk and surface properties as the synthesized array, for example, electrical properties, including super- and semi-conductivity, and thermal, mechanical, thermoelectric, optical, optoelectronic, fluorescent and/or biological properties, including immunogenicity.

Discovery and characterization of materials often requires combinatorial deposition onto substrates of thin films of precisely known chemical composition, concentration, stoichiometry, area and/or thickness. Devices and methods for making arrays of different materials, each with differing composition, concentration, stoichiometry and thin-layer thickness at known substrate locales, permitting systematic combinatorial array based synthesis and analysis that utilize thin layer deposition methods, are already known. Although existing thin-layer methods have been effectively used in precisely delivering reagent so as to make arrays of different materials, the predefinition required in these synthetic techniques is inflexible, and the techniques are slow and thus relatively costly. Additionally, thin-layer techniques are inherently less suited to creating experimental materials under conditions that deviate drastically from conditions that are thermodynamically reversible or nearly so. Thus, a need exists for more efficient and rapid delivery of precise amounts of reagents needed for materials array preparation, with more flexibility as to predetermination and conditions of formation than attainable by thin-layer methods.

In combinatorial synthesis of biomacromolecules, U.S. Pat. Nos. 5,700,637 and 6,054,270 to Southern et al., as noted previously, describe a method for generating an array of oligonucleotides of chosen monomeric unit length within discrete cells or regions of a support material. The in situ method generally described for oligo- or polynucleotide synthesis involves: coupling a nucleotide precursor to a discrete predetermined set of cell locations or regions; coupling a nucleotide precursor to a second set of cell locations or regions; coupling a nucleotide precursor to a third set of cell locations or regions; and continuing the sequence of coupling steps until the desired array has been generated. Covalent linking is effected at each location either to the surface of the support or to a nucleotide coupled in a previous step.

The '637 and '270 patents also teach that impermeable substrates are preferable to permeable substrates, such as paper, for effecting high combinatorial site densities, because the fluid volumes required will result in migration or wicking through a permeable substrate, precluding attainment of the small feature sizes required for high densities (such as those that are attainable by parallel photolithographic synthesis, which requires a substrate that is optically smooth and generally also impermeable; see U.S. Pat. No. 5,744,305 to Fodor et al.). As the inkjet printing method is a parallel synthesis technique that requires the array to be "predetermined" in nature, and therefore inflexible, and does not enable feature sites in the micron range or smaller, there remains a need in the art for a non-photolithographic in situ combinatorial array preparation method that can provide the high densities attainable by photolithographic arrays, a feat that requires small volumes of reagents and a highly accurate deposition method, without the inflexibility of a highly parallel process that requires a predetermined site sequence. Also, as permeable substrates offer a greater surface area for localization of array constituents, a method of effecting combinatorial high density arrays non-photolithographically by delivery of sufficiently small volumes to permit use of permeable substrates is also an advance over the current state of the art of array making.

As explained above, the parallel photolithographic in situ formation of biomolecular arrays of high density, e.g., oligonucleotide or polynucleotide arrays, is also known in the art. For example, U.S. Pat. Nos. 5,744,305 and 5,445,934 to Fodor et al. describe arrays of oligonucleotides and polynucleotides attached to a surface of a planar non-porous solid support at a density exceeding 400 and 1000 different oligonucleotides/cm² respectively. The arrays are generated using light-directed, spatially addressable synthesis techniques (see also U.S. Pat. Nos. 5,143,854 and 5,405,783, and International Patent Publication No. WO 90/15070). With respect to these photolithographic parallel in situ synthesized microarrays, Fodor et al. have developed photolabile nucleoside and peptide protecting groups, and masking and automation techniques; see U.S. Pat. No. 5,489,678 and International Patent Publication No. WO 92/10092).

The aforementioned patents disclose that photolithographic techniques commonly used in semiconductor fabrication may be applied in the fabrication of arrays of high density. Photolithographic in situ synthesis is best for parallel synthesis, requiring an inordinate number of masking steps to effect a sequential in situ combinatorial array synthesis. Even the parallel combinatorial array synthesis employing a minimized number of masking steps employs a significant number of such steps, which increases for each monomeric unit added in the synthesis. Further, the parallel photolithographic in situ array synthesis is inflexible and requires a predetermined mask sequence.

As photolithographic fabrication requires a large number of masking steps, the yield for this process is lowered relative to a non-photolithographic in situ synthesis by the failure to block and/or inappropriate photo-deblocking by some of the photolabile protective groups. These problems with photolabile protective groups compound the practical yield problem for multi-step in situ syntheses in general by adding photochemical steps to the synthetic process. The problems have not been addressed by the advances made in the art of making and using such photolabile blockers for in situ synthesis, in part because some photolabile blocking groups are shielded from the light or "buried" by the polymer on which they reside, an effect exacerbated with increasing polymer length. Therefore, the purity of the desired product is low, as the array will contain significant impurities of undesired products that can reduce both sensitivity and selectivity.

As the photolithographic process for in situ synthesis defines site edges with mask lines, mask imperfections and misalignment, diffractive effects and perturbations of the optical smoothness of the substrate can combine to reduce purity by generating polymers similar in sequence and/or structure to the desired polymer as impurities, a problem that becomes more pronounced at the site edges. This is exacerbated when photolithographic protocols attempt to maximize site density by creating arrays that have abutting sites. Because the likelihood of a mask imperfection or misalignment increases with the number of masking steps and the associated number of masks, these edge effects are exacerbated by an increased number of masking steps and utilization of more mask patterns to fabricate a particular array. Site impurity, i.e., generation of polymers similar in sequence and/or structure to the desired polymer, leads to reduced sensitivity and selectivity for arrays designed to analyze a nucleotide sequence.

Some efforts have been directed to adapting printing technologies, particularly, inkjet printing technologies, to form biomolecular arrays. For example, U.S. Pat. No. 6,015,880 to Baldeschwieler et al. is directed to array preparation using a multistep in situ synthesis. A liquid microdrop containing a first reagent is applied by a single jet of a multiple jet reagent dispenser to a locus on the surface chemically prepared to permit covalent attachment of the reagent. The reagent dispenser is then displaced relative to the surface, or the surface is displaced with respect to the dispenser, and at least one microdrop containing either the first reagent or a second reagent from another dispenser jet is applied to a second substrate locale, which is also chemically activated to be reactive for covalent attachment of the second reagent. Optionally, the second step is repeated using either the first or second reagents, or different liquid-borne reagents from different dispenser jets, wherein each reagent covalently attaches to the substrate surface. The patent discloses that inkjet technology may be used to apply the microdrops.

Ordinary inkjet technology, however, suffers from a number of drawbacks. Often, inkjet technology involves heating or using a piezoelectric element to force a fluid through a nozzle in order to direct the ejected fluid onto a surface. Thus, the fluid may be exposed to a surface exceeding 200° C. before being ejected, and most, if not all, peptidic molecules, including proteins, degrade under such extreme temperatures. In addition, forcing peptidic molecules through nozzles creates shear forces that can alter molecular structure. Nozzles are subject to clogging, especially when used to eject a macromolecule-containing fluid, and the use of elevated temperatures exacerbates the problem because liquid evaporation results in deposition of precipitated solids on the nozzles. Clogged nozzles, in turn, can result in misdirected fluid or ejection of improperly sized droplets. Finally, ordinary inkjet technology employing a nozzle for fluid ejection generally cannot be used to deposit arrays with feature densities comparable to those obtainable using photolithography or other techniques commonly used in semiconductor processing.

A number of patents have described the use of acoustic energy in printing. For example, U.S. Pat. No. 4,308,547 to Lovelady et al. describes a liquid drop emitter that utilizes acoustic principles in ejecting droplets from a body of liquid onto a moving document to form characters or bar codes thereon. A nozzleless inkjet printing apparatus is used wherein controlled drops of ink are propelled by an acoustical force produced by a curved transducer at or below the surface of the ink. In contrast to inkjet printing devices, nozzleless fluid ejection devices described in the aforementioned patent are not subject to clogging and the disadvantages associated therewith, e.g., misdirected fluid or improperly sized droplets.

The applicability of nozzleless fluid ejection has generally been appreciated for ink printing applications. Development of ink printing applications is primarily driven by cost as well as the need to print acceptable text rapidly. For acoustic printing, development efforts have therefore focused on reducing printing costs rather than improving quality, and on increasing printing speed rather than accuracy. For example, U.S. Pat. No. 5,087,931 to Rawson is directed to a system for transporting ink under constant flow to an acoustic ink printer having a plurality of ejectors aligned along an axis, each ejector associated with a free surface of liquid ink. When a plurality of ejectors is used instead of a single ejector, printing speed generally increases, but controlling fluid ejection, specifically droplet placement, becomes more difficult.

U.S. Pat. No. 4,797,693 to Quate describes an acoustic ink printer for printing polychromatic images on a recording medium. The printer is described as comprising a combination of a carrier containing a plurality of differently colored liquid inks, a single acoustic printhead acoustically coupled to the carrier for launching converging acoustic waves into the carrier, an ink transport means to position the carrier to sequentially align the differently colored inks with the printhead, and a controller to modulate the radiation pressure used to eject ink droplets. This printer is described as designed for the realization of cost savings. Because two droplets of primary color, e.g., cyan and yellow, deposited in sufficient proximity will appear as a composite or secondary color, the level of accuracy required is fairly low and inadequate for biomolecular array formation. Such a printer is particularly unsuitable for in situ synthesis requiring precise droplet deposition and consistent placement, so that the proper chemical reactions occur. That is, the drop placement accuracy needed to effect perception of a composite secondary color is much lower than is required for chemical synthesis at photolithographic density levels. Consequently, an acoustic printing device that is suitable for printing visually apprehensible material is inadequate for microarray preparation. Also, this device can eject only a limited quantity of ink from the carrier before the liquid meniscus moves out of acoustic focus and drop ejection ceases. This is a significant limitation with biological fluids, which are typically far more costly and rare than ink. The Quate et al. patent does not address how to use most of the fluid in a closed reservoir without adding additional liquid from an external source.

Thus, there is a general need in the art of combinatorial array preparation for improved spatially directable fluid ejection methods having sufficient droplet ejection accuracy to permit attainment of high density arrays of combinatorial materials made from a diverse group of starting materials. Specifically, acoustic fluid ejection devices as described herein can effect improved spatial direction of fluid ejection without the disadvantages of lack of flexibility and uniformity associated with photolithographic techniques or inkjet printing devices effecting droplet ejection through a nozzle.

One of the advantages of nozzleless acoustic ejection is the ability to reduce shear forces in the fluid, while obtaining better control over droplet volume and a smaller minimum volume. These advantages also apply relative to the conventional microfluidic channel manipulation of fluids. The reduction of shear forces is an important advantage for manipulating macromolecule solutes in a fluid, and especially conformationally complex and labile biomacromolecules such as proteins and nucleic acids having higher order structure than primary structure.

Crystallographic considerations and applications: Understanding the three-dimensional structure of proteins is critical to understanding mechanisms of protein binding to other proteins and other ligands, including small molecules, polynucleotides, oligonucleotides, and other moieties of interest. There is thus a great demand for rapid, high-resolution protein structure determination by x-ray crystallography. Advances in computational capability, together with the availability of high-intensity x-ray sources (such as synchrotrons) and charge coupled device (CCD) detectors, have drastically reduced the amount of time required to obtain a crystal structure. Synchrotron radiation and CCD detectors also permit smaller crystals to be used for crystallographic experiments than those required by other methods. A significant impediment to protein structure determination is the inability to rapidly screen protein crystallization methods, which could lead to the rapid production of high quality protein crystals.

The conditions under which high-quality protein crystals (i.e., those suitable for high-resolution single-crystal x-ray crystallography) form are largely unpredictable. Consequently, combinatorial methodologies that screen many combinations of crystallization parameters in parallel should be useful in determining the optimal crystallization parameters for producing high-quality protein crystals.

Parameters for crystallization experiments include temperature, pH, ionic strength, molecular weight, concentrations of various solvents, percent of organic components such as dimethyl sulfoxide, protein concentration, and concentrations of macromolecule and small moiety co-crystal components. Given such a large set of parameters, it is impracticable to rapidly screen each possible permutation by conventionally employed methods. Moreover, even using recombinant technology for protein expression, supplies of pure proteins for crystallization are usually limited, which limits the number of combinations that can be tested and reduces the chances for successful crystallization. A significant need therefore exists for combinatorial methods of experimentation to determine optimal conditions for protein crystallization, to increase the rapidity of screening and reduce the amount of protein required for each experiment.

A further problem in high-throughput crystallization is detecting nascent protein crystals. The observation of crystals in a solution does not guarantee the presence of protein crystals suitable for high-resolution x-ray crystallography. Salts in the buffer solution may crystallize instead of the desired protein. Current visual inspection methods are usually not able to distinguish between buffer crystals and protein crystals because sizes and morphologies of these crystals overlap. Distinguishing buffer crystals from protein crystals often requires mounting crystals in a diffractometer, an inefficient method of screening that requires removal of crystals from the wells and manual mounting. Such handling of crystals increases the probability of cracking, melting, or otherwise damaging the crystals prior to data acquisition.

Thus a need exists for small volume crystallization experiments to conserve moieties of interest for crystallization, especially biomacromolecules, and permit more experiments for a given amount of sample. A further need exists for speeding the successful production of high-quality crystals. Further, a need exists for determining whether crystals of the desired moiety have crystallized; specifically, in the context of biomacromolecule crystallization, whether biomacromolecule or non-biomacromolecule crystals have formed. Finally, a need exists for the in situ determination of whether crystals are of sufficient quality for high-resolution x-ray crystallography.

SUMMARY OF THE INVENTION

Accordingly, it is an object of the present invention to provide methods for detecting crystallization events and analyzing the characteristics of a formed crystal, using very small volumes of reagents and materials.

In one aspect of the invention, a method is provided is provided for generating a small volume of fluid containing a moiety of interest for crystallization and having a known composition, comprising acoustically depositing one or more reagent-containing fluid droplets at a site on a substrate surface, wherein at least one of the reagent-containing fluid droplets deposited at the site contains the moiety of interest for crystallization and at least one of the reagent-containing fluid droplets contains an agent that increases the likelihood of crystal formation.

A preferred device for carrying out the method is a focused acoustic ejection device described in U.S. patent application Ser. Nos. 09/669,996 and 09/964,212 ("Acoustic Ejection of Fluids from a Plurality of Reservoirs"), inventors Ellson, Foote, and Mutz, filed on Sep. 25, 2000, and Sep. 25, 2001, respectively, and assigned to Picoliter, Inc. (Mountain View, Calif.). As described in the aforementioned patent applications, the device enables acoustic ejection of a plurality of fluid droplets toward designated sites on a substrate surface for deposition thereon, and comprises: a plurality of reservoirs each adapted to contain a fluid; an acoustic ejector that includes an acoustic radiation generator and a focusing means for focusing the generated acoustic radiation at a focal point sufficiently near the fluid surface in each of the reservoirs such that droplets are ejected therefrom; and a means for positioning the ejector in acoustic coupling relationship to each of the reservoirs. Preferably, each of the reservoirs is removable, comprised of an individual well in a well plate, and/or arranged in an array. The reservoirs are preferably also substantially acoustically indistinguishable from one another, have appropriate acoustic impedance and attenuation to allow the energetically efficient focusing of acoustic energy near the surface of a contained fluid, and are capable of withstanding conditions of the fluid-containing reagent.

In a related aspect of the invention, a method is provided for detecting crystals formed following the above-described process. The method involves, as above, generating a small volume of fluid containing a moiety of interest for crystallization and having a known composition, comprising (a) depositing one or more reagent-containing fluid droplets at a site on a substrate surface by focused energy ejection, at least one of the reagent-containing fluid droplets deposited at the site containing the moiety of interest for crystallization, and (b) detecting the presence and quantity of crystalline material composed of the moiety of interest in the small fluid volume at the site. Preferably, although not necessarily, step (b) of the method is carried out acoustically, as will be described in detail herein.

In another aspect of the invention, a system is provided for conducting combinatorial experiments to crystallize a moiety of interest and detect crystallization thereof. The system includes: a substrate having a plurality of discrete sites; a plurality of reservoirs each adapted to contain a reagent-containing fluid; an ejector comprising an acoustic radiation generator for generating acoustic radiation and a focusing means for focusing the acoustic radiation at a focal point near the fluid surface in each of the reservoirs; a means for positioning the ejector in acoustic coupling relationship to each of the reservoirs; and means for detecting crystallization of the moiety of interest; wherein one or more of the materials arrayed on the substrate are contacted with one or more reagent-containing fluids by acoustic ejection, and any physical or chemical change detected at a site upon said contacting denotes a screening result for the material present at the site contacted with said one or more reagent-containing fluids. Preferably, the detecting means involves acoustic detection. Also, it is preferred that the device include a means for ascertaining the quality of any crystals formed, preferably a means that involves x-ray diffraction, scanning, diffractometry, or light scattering.

Yet another aspect of the invention provides high density arrays of small fluid volumes that have a known composition and contain a moiety of interest for crystallization, typically although not necessarily a biomolecule, with each volume contained within a discrete site on a substrate surface divided into a plurality of discrete sites, with each site not containing more than a single fluid volume. The present focused acoustic ejection methodology enables preparation of arrays comprised of at least 100, preferably at least about 1000, more preferably at least about 62,500, still more preferably at least about 250,000, still more preferably at least about 1,000,000, and most preferably at least about 1,500,000 elements per square centimeter of substrate surface. These arrays do not possess the edge effects that result from optical and alignment effects of photolithographic masking, nor are they subject to imperfect spotting alignment from inkjet nozzle-directed deposition of reagents.

BRIEF DESCRIPTION OF THE DRAWINGS

FIG. 1A shows the acoustic ejector acoustically coupled to the first reservoir and having been activated in order to eject a droplet of fluid from within the first reservoir toward a designated site on a substrate surface.

FIG. 1B shows the acoustic ejector acoustically coupled to a second reservoir.

FIG. 2A is a schematic top plan view of the two well plates, i.e., the reservoir well plate and the substrate well plate.

FIG. 2B illustrates in cross-sectional view a device comprising the reservoir well plate of FIG. 2A acoustically coupled to an acoustic ejector, wherein a droplet is ejected from a first well of the reservoir well plate into a first well of the substrate well plate.

FIG. 2C illustrates in cross-sectional view the device illustrated in FIG. 2B, wherein the acoustic ejector is acoustically coupled to a second well of the reservoir well plate and further wherein the device is aligned to enable the acoustic ejector to eject a droplet from the second well of the reservoir well plate to a second well of the substrate well plate.

FIG. 3A illustrates the ejection of a droplet of surface modification fluid onto a designated site of a substrate surface.

FIG. 3B illustrates the ejection of a droplet of a first fluid containing a first molecular moiety adapted for attachment to the modified surface of the substrate.

FIG. 3C illustrates the ejection of a droplet of a second fluid containing a second molecular moiety adapted for attachment to the first molecule.

FIG. 3D illustrates the substrate and the dimer synthesized in situ by the process illustrated in FIGS. 3A, 3B, and 3C.

FIG. 4A depicts a standing drop container without the cover slip in place.

FIG. 4B depicts a fully assembled standing drop container with a filled fluid reservoir and a standing drop that is covered by a cover slip and sealed.

FIG. 4C depicts a fully assembled hanging drop protein crystallization container with a single experimental protein crystallization drop hanging above the fluid reservoir.

DETAILED DESCRIPTION OF THE INVENTION

Figure 1A:
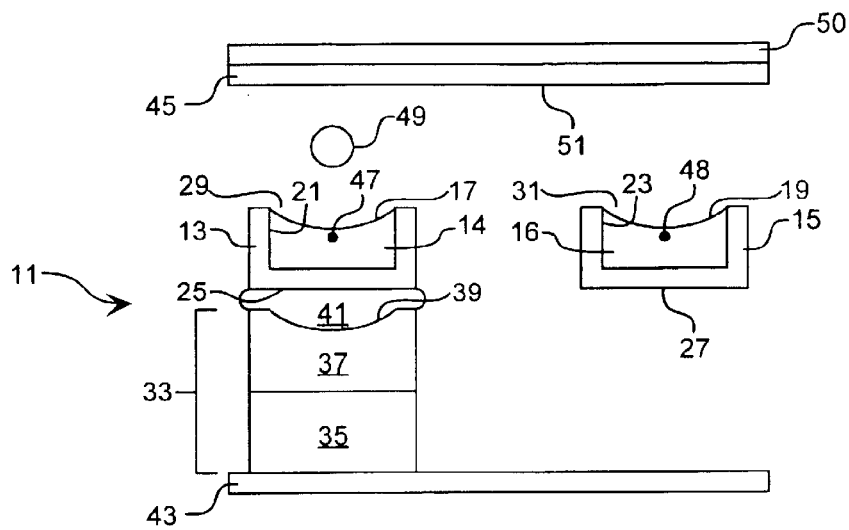
FIGS. 1A and 1B, collectively referred to as FIG. 1, schematically illustrate in simplified cross-sectional view an embodiment of a device useful in conjunction with the method of the invention, the device comprising first and second reservoirs, an acoustic ejector, and an ejector positioning means.

Before describing the present invention in detail, it is to be understood that this invention is not limited to specific fluids, biomolecules, or device structures, as such may vary. It is also to be understood that the terminology used herein is for the purpose of describing particular embodiments only, and is not intended to be limiting.

Before describing the present invention in detail, it is to be understood that this invention is not limited to specific fluids, biomolecules or device structures, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a reservoir" includes a single reservoir as well as a plurality of reservoirs, reference to "a fluid" includes a single fluid as well as a plurality and/or mixture of two or more different fluids, reference to "a biomolecule" includes a single biomolecule as well as a combination of biomolecules, "a moiety" can refer to a plurality of moieties, and the like.

In describing and claiming the present invention, the following terminology will be used in accordance with the definitions set out below.

The terms "acoustic coupling" and "acoustically coupled" used herein refer to a state wherein an object is placed in direct or indirect contact with another object so as to allow acoustic radiation to be transferred between the objects without substantial loss of acoustic energy. When two entities are indirectly acoustically coupled, an "acoustic coupling medium" is needed to provide an intermediary through which acoustic radiation may be transmitted. Thus, an ejector may be acoustically coupled to a fluid, e.g., by immersing the ejector in the fluid or by interposing an acoustic coupling medium between the ejector and the fluid to transfer acoustic radiation generated by the ejector through the acoustic coupling medium and into the fluid.

The term "adsorb" as used herein refers to the noncovalent retention of a molecule by a substrate surface. That is, adsorption occurs as a result of noncovalent interaction between a substrate surface and adsorbing moieties present on the molecule that is adsorbed. Adsorption may occur through hydrogen bonding, van der Waal's forces, polar attraction or electrostatic forces (i.e., through ionic bonding). Examples of adsorbing moieties include, but are not limited to, amine groups, carboxylic acid moieties, hydroxyl groups, nitroso groups, sulfones and the like. Often the substrate may be functionalized with adsorbent moieties to interact in a certain manner, as when the surface is functionalized with amino groups to render it positively charged in a pH neutral aqueous environment. Likewise, adsorbate moieties may be added in some cases to effect adsorption, as when a basic protein is fused with an acidic peptide sequence to render adsorbate moieties that can interact electrostatically with a positively charged adsorbent moiety.

The term "attached," as in, for example, a substrate surface having a moiety "attached" thereto, includes covalent binding, adsorption, and physical immobilization. The terms "binding" and "bound" are identical in meaning to the term "attached."

The term "array" used herein refers to a two-dimensional arrangement of features such as an arrangement of reservoirs (e.g., wells in a well plate) or an arrangement of different materials including ionic, metallic or covalent crystalline, including molecular crystalline, composite or ceramic, glassine, amorphous, fluidic or molecular materials on a substrate surface (as in an oligonucleotide or peptidic array). Different materials in the context of molecular materials includes chemical isomers, including constitutional, geometric and stereoisomers, and in the context of polymeric molecules constitutional isomers having different monomer sequences. Arrays are generally comprised of regular, ordered features, as in, for example, a rectilinear grid, parallel stripes, spirals, and the like, but non-ordered arrays may be advantageously used as well. An array is distinguished from the more general term "pattern" in that patterns do not necessarily contain regular and ordered features. The arrays or patterns formed using the devices and methods of the invention have no optical significance to the unaided human eye. For example, the invention does not involve ink printing on paper or other substrates in order to form letters, numbers, bar codes, figures, or other inscriptions that have optical significance to the unaided human eye. In addition, arrays and patterns formed by the deposition of ejected droplets on a surface as provided herein are preferably substantially invisible to the unaided human eye. The arrays prepared using the method of the invention generally comprise in the range of about 4 to about 10,000,000 features, more typically about 4 to about 1,000,000 features.

The terms "biomolecule" and "biological molecule" are used interchangeably herein to refer to any organic molecule, whether naturally occurring, recombinantly produced, or chemically synthesized in whole or in part, that is, was or can be a part of a living organism. The terms encompass, for example, nucleotides, amino acids and monosaccharides, as well as oligomeric and polymeric species such as oligonucleotides and polynucleotides, peptidic molecules such as oligopeptides, polypeptides and proteins, saccharides such as disaccharides, oligosaccharides, polysaccharides, mucopolysaccharides or peptidoglycans (peptido-polysaccharides) and the like. The term also encompasses ribosomes, enzyme cofactors, pharmacologically active agents, and the like.

The term "biomaterial" refers to any material that is biocompatible, i.e., compatible with a biological system comprised of biological molecules as defined above.

The terms "library" and "combinatorial library" are used interchangeably herein to refer to a plurality of chemical or biological moieties present on the surface of a substrate, wherein each moiety is different from each other moiety. The moieties may be, e.g., peptidic molecules and/or oligonucleotides.

The term "moiety" refers to any particular composition of matter, e.g., a molecular fragment, an intact molecule (including a monomeric molecule, an oligomeric molecule, and a polymer), or a mixture of materials (for example, an alloy or a laminate).

It will be appreciated that, as used herein, the terms "nucleoside" and "nucleotide" refer to nucleosides and nucleotides containing not only the conventional purine and pyrimidine bases, i.e., adenine (A), thymine (T), cytosine (C), guanine (G) and uracil (U), but also protected forms thereof, e.g., wherein the base is protected with a protecting group such as acetyl, difluoroacetyl, trifluoroacetyl, isobutyryl or benzoyl, and purine and pyrimidine analogs. Suitable analogs will be known to those skilled in the art and are described in the pertinent texts and literature. Common analogs include, but are not limited to, 1-methyladenine, 2-methyladenine, N⁶-methyladenine, N⁶-isopentyladenine, 2-methylthio-N⁶-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

As used herein, the term "oligonucleotide" shall be generic to polydeoxynucleotides (containing 2-deoxy-D-ribose), to polyribonucleotides (containing D-ribose), to any other type of polynucleotide that is an N-glycoside of a purine or pyrimidine base, and to other polymers containing normucleotidic backbones (for example PNAs), providing that the polymers contain nucleobases in a configuration that allows for base pairing and base stacking, such as is found in DNA and RNA. Thus, these terms include known types of oligonucleotide modifications, for example, substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.). There is no intended distinction in length between the term "polynucleotide" and "oligonucleotide," and these terms will be used interchangeably. These terms refer only to the primary structure of the molecule. As used herein the symbols for nucleotides and polynucleotides are according to the IUPAC-IUB Commission of Biochemical Nomenclature recommendations (*Biochemistry* 9:4022, 1970).

The terms "peptide," "peptidyl" and "peptidic" as used throughout the specification and claims are intended to include any structure comprised of two or more amino acids. For the most part, the peptides in the present arrays comprise about 5 to 10,000 amino acids, preferably about 5 to 1000 amino acids. The amino acids forming all or a part of a peptide may be any of the twenty conventional, naturally occurring amino acids, i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y). Any of the amino acids in the peptidic molecules forming the present arrays may be replaced by a non-conventional amino acid. In general, conservative replacements are preferred. Conservative replacements substitute the original amino acid with a non-conventional amino acid that resembles the original in one or more of its characteristic properties (e.g., charge, hydrophobicity, stearic bulk; for example, one may replace Val with Nval). The term "non-conventional amino acid" refers to amino acids other than conventional amino acids, and include, for example, isomers and modifications of the conventional amino acids (e.g., D-amino acids), non-protein amino acids, post-translationally modified amino acids, enzymatically modified amino acids, constructs or structures designed to mimic amino acids (e.g., α,α-disubstituted amino acids, N-alkyl amino acids, lactic acid, β-alanine, naphthylalanine, 3-pyridylalanine, 4-hydroxyproline, O-phosphoserine, N-acetylserine, N-formylmethionine, 3-methylhistidine, 5-hydroxylysine, and norleucine), and peptides having the naturally occurring amide—CONH—linkage replaced at one or more sites within the peptide backbone with a non-conventional linkage such as N-substituted amide, ester, thioamide, retropeptide (—NHCO—), retrothioamide (—NHCS—), sulfonamido (—SO₂NH—), and/or peptoid (N-substituted glycine) linkages. Accordingly, the peptidic molecules of the array include pseudopeptides and peptidomimetics. The peptides of this invention can be (a) naturally occurring, (b) produced by chemical synthesis, (c) produced by recombinant DNA technology, (d) produced by biochemical or enzymatic fragmentation of larger molecules, (e) produced by methods resulting from a combination of methods (a) through (d) listed above, or (f) produced by any other means for producing peptides.

The term "fluid" as used herein refers to matter that is nonsolid or at least partially gaseous and/or liquid. A fluid may contain a solid that is minimally, partially or fully solvated, dispersed or suspended. Examples of fluids include, without limitation, aqueous liquids (including water per se and salt water) and nonaqueous liquids such as organic solvents and the like. As used herein, the term "fluid" is not synonymous with the term "ink" in that an ink must contain a colorant and may not be gaseous and/or liquid.

The term "near" is used to refer to the distance from the focal point of the focused acoustic radiation to the surface of the fluid from which a droplet is to be ejected. The distance should be such that the focused acoustic radiation directed into the fluid results in droplet ejection from the fluid surface, and one of ordinary skill in the art will be able to select an appropriate distance for any given fluid using straightforward and routine experimentation. Generally, however, a suitable distance between the focal point of the acoustic radiation and the fluid surface is in the range of about 1 to about 15 times the wavelength of the acoustic radiation in the fluid, more typically in the range of about 1 to about 10 times that wavelength, preferably in the range of about 1 to about 5 times that wavelength.

The terms "focusing means" and "acoustic focusing means" refer to a means for causing acoustic waves to converge at a focal point by either a device separate from the acoustic energy source that acts like an optical lens, or by the spatial arrangement of acoustic energy sources to effect convergence of acoustic energy at a focal point by constructive and destructive interference. A focusing means may be as simple as a solid member having a curved surface, or it may include complex structures such as those found in Fresnel lenses, which employ diffraction in order to direct acoustic radiation. Suitable focusing means also include phased array methods as known in the art and described, for example, in U.S. Pat. No. 5,798,779 to Nakayasu et al. and Amemiya et al. (1997) *Proceedings of the 1997 IS&T NIP13 International Conference on Digital Printing Technologies Proceedings*, at pp. 698–702.

The term "reservoir" as used herein refers to a receptacle or chamber for holding or containing a fluid. Thus, a fluid in a reservoir necessarily has a free surface, i.e., a surface that allows a droplet to be ejected therefrom. A reservoir may also be a locus on a substrate surface within which a fluid is constrained.

The term "substrate" as used herein refers to any material having a surface onto which one or more fluids may be deposited. The substrate may be constructed in any of a number of forms such as wafers, slides, well plates, membranes, for example. In addition, the substrate may be porous or nonporous as may be required for deposition of a particular fluid. Suitable substrate materials include, but are not limited to, supports that are typically used for solid phase chemical synthesis, e.g., polymeric materials (e.g., polystyrene, polyvinyl acetate, polyvinyl chloride, polyvinyl pyrrolidone, polyacrylonitrile, polyacrylamide, polymethyl methacrylate, polytetrafluoroethylene, polyethylene, polypropylene, polyvinylidene fluoride, polycarbonate, divinylbenzene styrene-based polymers), agarose (e.g., Sepharose®), dextran (e.g., Sephadex®), cellulosic polymers and other polysaccharides, silica and silica-based materials, glass (particularly controlled pore glass, or "CPG") and functionalized glasses, ceramics, and such substrates treated with surface coatings, e.g., with microporous polymers (particularly cellulosic polymers such as nitrocellulose), microporous metallic compounds (particularly microporous aluminum), antibody-binding proteins (available from Pierce Chemical Co., Rockford Ill.), bisphenol A polycarbonate, or the like.

Substrates may be porous, and porous substrates include, as alluded to above: uncoated porous glass slides, including CPG slides; porous glass slides coated with a polymeric coating, e.g., an aminosilane or poly-L-lysine coating, thus having a porous polymeric surface; and nonporous glass slides coated with a porous coating. The porous coating may be a porous polymer coating, such as may be comprised of a cellulosic polymer (e.g., nitrocellulose) or polyacrylamide, or a porous metallic coating (for example, comprised of microporous aluminum). Examples of commercially available substrates having porous surfaces include the Fluorescent Array Surface Technology (FAST™) slides available from Schleicher & Schuell, Inc. (Keene, N. H.), which are coated with a 10–30 µm thick porous, fluid-permeable nitrocellulose layer that substantially increases the available binding area per unit area of surface. Other commercially available porous substrates include the CREATIVECHIP® permeable slides currently available from Eppendorf AG (Hamburg, Germany), and substrates having "three-dimensional" geometry, by virtue of an ordered, highly porous structure that enables reagents to flow into and penetrate through the pores and channels of the entire structure. Such substrates are available from Gene Logic, Inc. under the tradename "Flow-Thru Chip," and are described by Steel et al. in Chapter 5 of *Microarray Biochip Technology* (BioTechniques Books, Natick, Mass., 2000).

The term "porous" as in a "porous substrate" or a "substrate having a porous surface," refers to a substrate or surface, respectively, having a porosity (void percentage) in the range of about 1% to about 99%, preferably about 5% to about 99%, more preferably in the range of about 15% to about 95%, and an average pore size of about 100 Å to about 1 mm, typically about 500 Å to about 0.5 mm.

The term "impermeable" is used in the conventional sense to mean not permitting water or other fluid to pass through. The term "permeable" as used herein means not "impermeable." Thus, a "permeable substrate" and a "substrate having a permeable surface" refer to a substrate or surface, respectively, which can be permeated with water or other fluid.

While the foregoing support materials are representative of conventionally used substrates, it is to be understood that a substrate may in fact comprise any biological, nonbiological, organic and/or inorganic material, and may be in any of a variety of physical forms, e.g., particles, strands, precipitates, gels, sheets, tubing, spheres, containers, capillaries, pads, slices, films, plates, and the like, and may further have any desired shape, such as a disc, square, sphere, circle, etc. The substrate surface may or may not be flat, e.g., the surface may contain raised or depressed regions. A substrate may additionally contain or be derivatized to contain reactive functionalities that covalently link a compound to the substrate surface. These are widely known and include, for example, silicon dioxide supports containing reactive Si—OH groups, polyacrylamide supports, polystyrene supports, polyethylene glycol supports, and the like.

The term "surface modification" as used herein refers to the chemical and/or physical alteration of a surface by an additive or subtractive process to change one or more chemical and/or physical properties of a substrate surface or a selected site or region of a substrate surface. For example, surface modification may involve (1) changing the wetting properties of a surface, (2) functionalizing a surface, i.e., providing, modifying or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface.

"Optional" or "optionally" means that the subsequently described circumstance may or may not occur, so that the description includes instances where the circumstance occurs and instances where it does not.

The term "substantially" as in, for example, the phrase "substantially all molecules of an array," refers to at least 90%, preferably at least 95%, more preferably at least 99%, and most preferably at least 99.9%, of the molecules of an array. Other uses of the term "substantially" involve an analogous definition.

In one embodiment, then, the invention pertains to a device for acoustically ejecting a plurality of droplets toward designated sites on a substrate surface. The device comprises a plurality of reservoirs, each adapted to contain a fluid; an ejector comprising an acoustic radiation generator for generating acoustic radiation and a focusing means for focusing acoustic radiation at a focal point within and near the fluid surface in each of the reservoirs; and a means for positioning the ejector in acoustic coupling relationship to each of the reservoirs. Preferably, none of the fluids is an ink.

FIG. 1 illustrates a suitable focused acoustic ejection device in simplified cross-sectional view. As with all figures referenced herein, in which like parts are referenced by like numerals, FIG. 1 is not to scale, and certain dimensions may be exaggerated for clarity of presentation. The device 11 includes a plurality of reservoirs, i.e., at least two reservoirs, with a first reservoir indicated at 13 and a second reservoir indicated at 15, each adapted to contain a fluid having a fluid surface, e.g., a first fluid 14 and a second fluid 16 having fluid surfaces respectively indicated at 17 and 19. Fluids 14 and 16 may be the same or different, and may also have acoustic or fluidic properties that are the same or different. As shown, the reservoirs are of substantially identical construction so as to be substantially acoustically indistinguishable, but identical construction is not a requirement. The reservoirs are shown as separate removable components but may, if desired, be fixed within a plate or other substrate. For example, the plurality of reservoirs may comprise individual wells in a well plate, optimally although not necessarily arranged in an array. Each of the reservoirs 13 and 15 is preferably axially symmetric as shown, having vertical walls 21 and 23 extending upward from circular reservoir bases 25 and 27 and terminating at openings 29 and 31, respectively, although other reservoir shapes may be used. The material and thickness of each reservoir base should be such that acoustic radiation may be transmitted therethrough and into the fluid contained within the reservoirs.

The device also includes an acoustic ejector 33 comprised of an acoustic radiation generator 35 for generating acoustic radiation and a focusing means 37 for focusing the acoustic radiation at a focal point within the fluid from which a droplet is to be ejected, near the fluid surface. As shown in FIG. 1, the focusing means 37 may comprise a single solid piece having a concave surface 39 for focusing acoustic radiation, but the focusing means may be constructed in other ways as discussed below. The acoustic ejector 33 is thus adapted to generate and focus acoustic radiation so as to eject a droplet of fluid from each of the fluid surfaces 17 and 19 when acoustically coupled to reservoirs 13 and 15 and thus to fluids 14 and 16, respectively. The acoustic radiation generator 35 and the focusing means 37 may function as a single unit controlled by a single controller, or they may be independently controlled, depending on the desired performance of the device. Typically, single ejector designs are preferred over multiple ejector designs because accuracy of droplet placement and consistency in droplet size and velocity are more easily achieved with a single ejector.

As will be appreciated by those skilled in the art, any of a variety of focusing means may be employed in conjunction with the present invention. For example, one or more curved surfaces may be used to direct acoustic radiation to a focal point near a fluid surface. One such technique is described in U.S. Pat. No. 4,308,547 to Lovelady et al. Focusing means with a curved surface have been incorporated into the construction of commercially available acoustic transducers such as those manufactured by Panametrics Inc. (Waltham, Mass.). In addition, Fresnel lenses are known in the art for directing acoustic energy at a predetermined focal distance from an object plane. See, e.g., U.S. Pat. No. 5,041,849 to Quate et al. Fresnel lenses may have a radial phase profile that diffracts a substantial portion of acoustic energy into a predetermined diffraction order at diffraction angles that vary radially with respect to the lens. The diffraction angles should be selected to focus the acoustic energy within the diffraction order on a desired object plane.

There are also a number of ways to acoustically couple the ejector 33 to each individual reservoir and thus to the fluid therein. One such approach is through direct contact as is described, for example, in U.S. Pat. No. 4,308,547 to Lovelady et al., wherein a focusing means constructed from a hemispherical crystal having segmented electrodes is submerged in a liquid to be ejected. The aforementioned patent further discloses that the focusing means may be positioned at or below the surface of the liquid. However, this approach for acoustically coupling the focusing means to a fluid is undesirable when the ejector is used to eject different fluids in a plurality of containers or reservoirs, as repeated cleaning of the focusing means would be required in order to avoid cross-contamination. The cleaning process would necessarily lengthen the transition time between each droplet ejection event. In addition, in such a method, fluid would adhere to the ejector as it is removed from each container, wasting material that may be costly or rare.

Thus, a preferred approach would be to acoustically couple the ejector to the reservoirs and reservoir fluids without contacting any portion of the ejector, e.g., the focusing means, with any of the fluids to be ejected. To this end, the present invention provides an ejector positioning means for positioning the ejector in controlled and repeatable acoustic coupling with each of the fluids in the reservoirs to eject droplets therefrom without submerging the ejector therein. This typically involves direct or indirect contact between the ejector and the external surface of each reservoir. When direct contact is used in order to acoustically couple the ejector to each reservoir, it is preferred that the direct contact is wholly conformal to ensure efficient acoustic energy transfer. That is, the ejector and the reservoir should have corresponding surfaces adapted for mating contact. Thus, if acoustic coupling is achieved between the ejector and reservoir through the focusing means, it is desirable for the reservoir to have an outside surface that corresponds to the surface profile of the focusing means. Without conformal contact, efficiency and accuracy of acoustic energy transfer may be compromised. In addition, since many focusing means have a curved surface, the direct contact approach may necessitate the use of reservoirs having a specially formed inverse surface.

Optimally, acoustic coupling is achieved between the ejector and each of the reservoirs through indirect contact, as illustrated in FIG. 1A. In the figure, an acoustic coupling medium 41 is placed between the ejector 33 and the base 25 of reservoir 13, with the ejector and reservoir located at a predetermined distance from each other. The acoustic coupling medium may be an acoustic coupling fluid, preferably an acoustically homogeneous material in conformal contact with both the acoustic focusing means 37 and each reservoir. In addition, it is important to ensure that the fluid medium is substantially free of material having different acoustic properties than the fluid medium itself. As shown, the first reservoir 13 is acoustically coupled to the acoustic focusing means 37 such that an acoustic wave is generated by the acoustic radiation generator and directed by the focusing means 37 into the acoustic coupling medium 41, which then transmits the acoustic radiation into the reservoir 13.

In operation, reservoirs 13 and 15 of the device are each filled with first and second fluids 14 and 16, respectively, as shown in FIG. 1. The acoustic ejector 33 is positionable by means of ejector positioning means 43, shown below reservoir 13, in order to achieve acoustic coupling between the ejector and the reservoir through acoustic coupling medium 41. Substrate 45 is positioned above and in proximity to the first reservoir 13 such that one surface of the substrate, shown in FIG. 1 as underside surface 51, faces the reservoir and is substantially parallel to the surface 17 of the fluid 14 therein. Once the ejector, the reservoir and the substrate are in proper alignment, the acoustic radiation generator 35 is activated to produce acoustic radiation that is directed by the focusing means 37 to a focal point 47 near the fluid surface 17 of the first reservoir. As a result, droplet 49 is ejected from the fluid surface 17 onto a designated site on the underside surface 51 of the substrate. The ejected droplet may be retained on the substrate surface by solidifying thereon after contact; in such an embodiment, it is necessary to maintain the substrate at a low temperature, i.e., a temperature that results in droplet solidification after contact. Alternatively, or in addition, a molecular moiety within the droplet attaches to the substrate surface after contract, through adsorption, physical immobilization, or covalent binding.

Figure 1B:
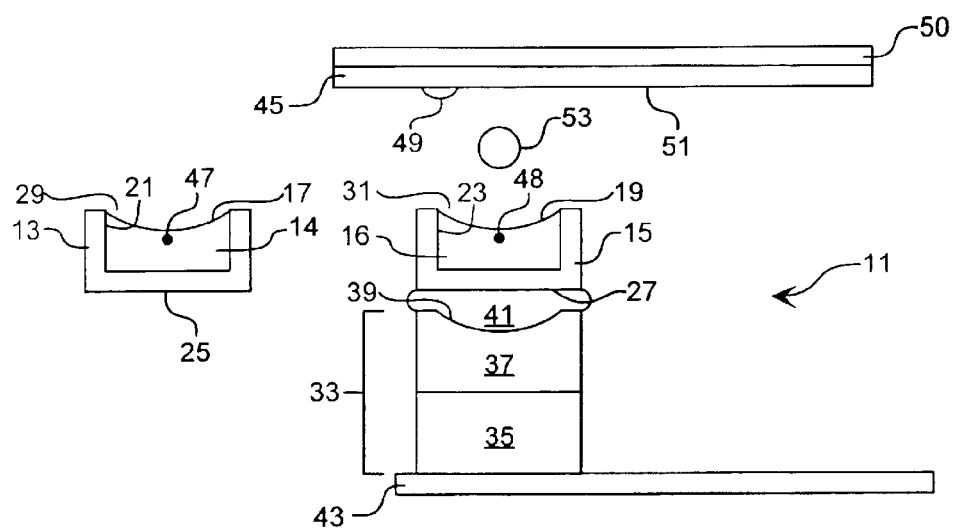

Then, as shown in FIG. 1B, a substrate positioning means 50 repositions the substrate 45 over reservoir 15 in order to receive a droplet therefrom at a second designated site. FIG. 1B also shows that the ejector 33 has been repositioned by the ejector positioning means 43 below reservoir 15 and in acoustically coupled relationship thereto by virtue of acoustic coupling medium 41. Once properly aligned as shown in FIG. 1B, the acoustic radiation generator 35 of ejector 33 is activated to produce acoustic radiation that is then directed by focusing means 37 to a focal point within fluid 16 near the fluid surface 19, thereby ejecting droplet 53 onto the substrate. It should be evident that such operation is illustrative of how the employed device may be used to eject a plurality of fluids from reservoirs in order to form a pattern, e.g., an array, on the substrate surface 51. It should be similarly evident that the device may be adapted to eject a plurality of droplets from one or more reservoirs onto the same site of the substrate surface.

Figure 2A:
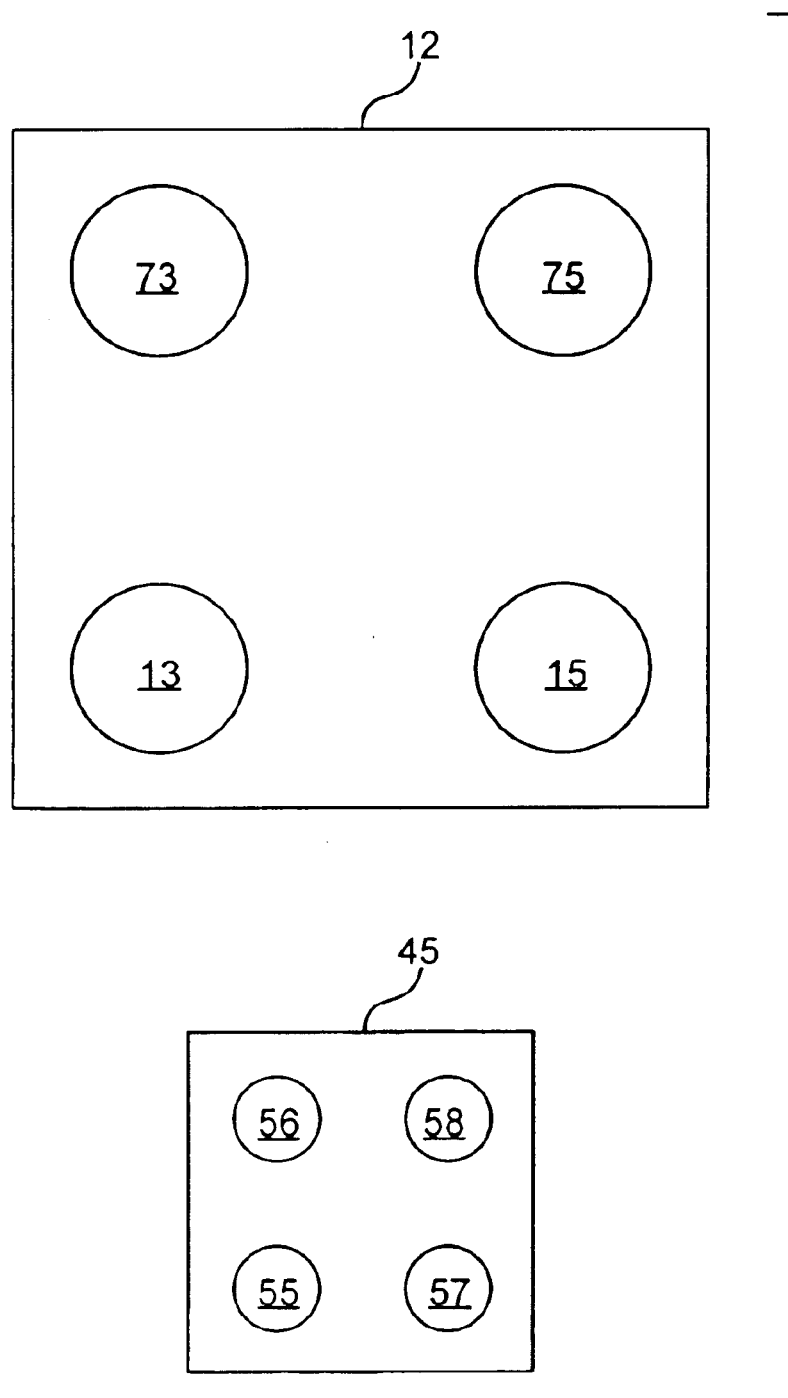
FIGS. 2A, 2B, and 2C, collectively referred to as FIG. 2, illustrate in schematic view a variation of the device shown in FIG. 1 wherein the reservoirs comprise individual wells in a reservoir well plate, and the substrate comprises a smaller well plate with a corresponding number of wells.
Figure 2B:
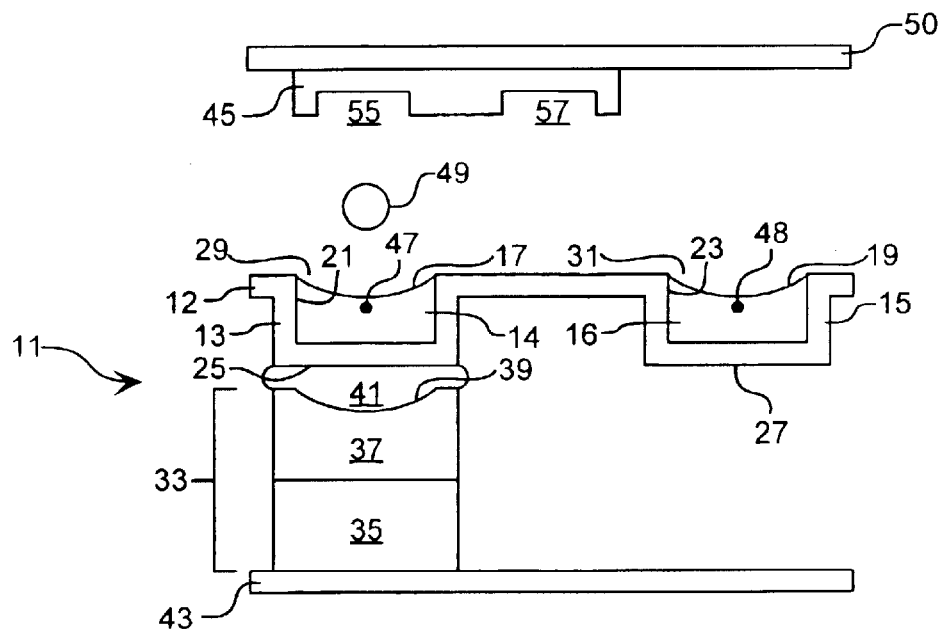

In another embodiment, the device is constructed so as to allow transfer of fluids between well plates, in which case the substrate comprises a substrate well plate, and the fluid-containing reservoirs are individual wells in a reservoir well plate. FIG. 2 illustrates such a device, wherein four individual wells 13, 15, 73 and 75 in reservoir well plate 12 serve as fluid reservoirs for containing a fluid to be ejected, and the substrate comprises a smaller well plate 45 of four individual wells indicated at 55, 56, 57 and 58. FIG. 2A illustrates the reservoir well plate and the substrate well plate in top plan view. As shown, each of the well plates contains four wells arranged in a two-by-two array. FIG. 2B illustrates the employed device wherein the reservoir well plate and the substrate well plate are shown in cross-sectional view along wells 13, 15 and 55, 57, respectively. As in FIG. 1, reservoir wells 13 and 15 respectively contain fluids 14 and 16 having fluid surfaces respectively indicated at 17 and 19. The materials and design of the wells of the reservoir well plate are similar to those of the reservoirs illustrated in FIG. 1. For example, the reservoir wells shown in FIG. 2B are of substantially identical construction so as to be substantially acoustically indistinguishable. In this embodiment as well, the bases of the reservoirs are of a material and thickness so as to allow efficient transmission of acoustic radiation therethrough into the fluid contained within the reservoirs.

The device of FIG. 2 also includes an acoustic ejector 33 having a construction similar to that of the ejector illustrated in FIG. 1, i.e., the ejector is comprised of an acoustic generating means 35 and a focusing means 37. FIG. 2B shows the ejector acoustically coupled to a reservoir well through indirect contact; that is, an acoustic coupling medium 41 is placed between the ejector 33 and the reservoir well plate 12, i.e., between the curved surface 39 of the acoustic focusing means 37 and the base 25 of the first reservoir well 13. As shown, the first reservoir well 13 is acoustically coupled to the acoustic focusing means 37 such that acoustic radiation generated in a generally upward direction is directed by the focusing mean 37 into the acoustic coupling medium 41, which then transmits the acoustic radiation into the reservoir well 13.

In operation, each of the reservoir wells is preferably filled with a different fluid.

As shown, reservoir wells 13 and 15 of the device are each filled with a first fluid 14 and a second fluid 16, as in FIG. 1, to form fluid surfaces 17 and 19, respectively. FIG. 2A shows that the ejector 33 is positioned below reservoir well 13 by an ejector positioning means 43 in order to achieve acoustic coupling therewith through acoustic coupling medium 41. The first substrate well 55 of substrate well plate 45 is positioned above the first reservoir well 13 in order to receive a droplet ejected from the first reservoir well. Once the ejector, the reservoir and the substrate are in proper alignment, the acoustic radiation generator is activated to produce an acoustic wave that is focused by the focusing means to direct the acoustic wave to a focal point 47 near fluid surface 17. As a result, droplet 49 is ejected from fluid surface 17 into the first substrate well 55 of the substrate well plate 45. The droplet is retained in the substrate well plate by surface tension or optionally by solidifying thereon after contact, by virtue of the low temperature at which the substrate well plate is maintained. That is, the substrate well plate is preferably associated with a cooling means (not shown) to maintain the substrate surface at a temperature that results in droplet solidification after contact.

Figure 2C:
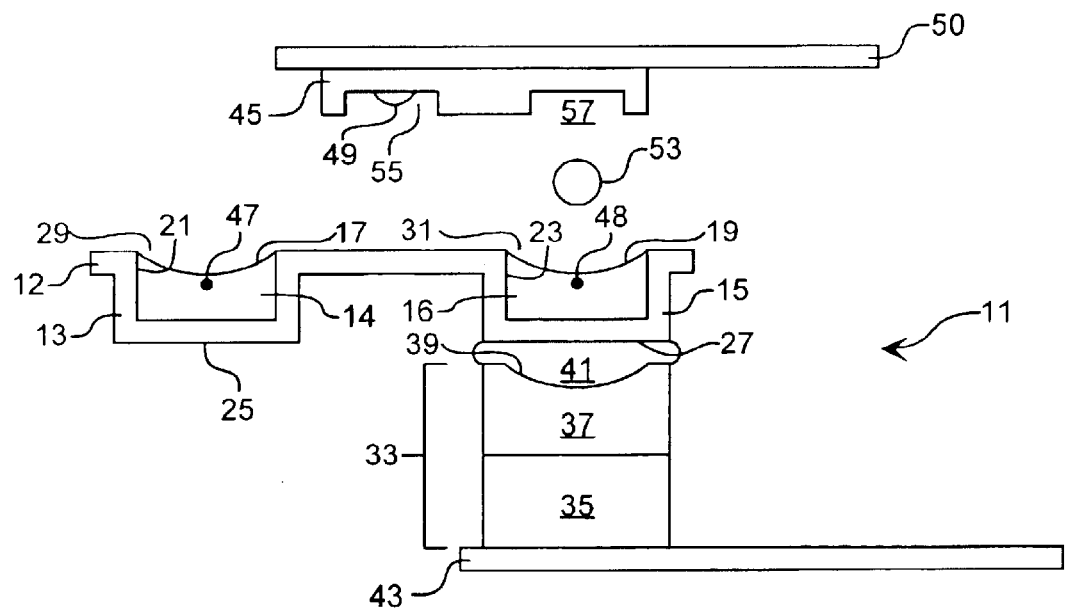

Then, as shown in FIG. 2C, the substrate well plate 45 is repositioned by a substrate positioning means 50 such that substrate well 57 is located directly over reservoir well 15 in order to receive a droplet therefrom. FIG. 2C also shows that the ejector 33 has been repositioned by the ejector positioning means below reservoir well 15 to acoustically couple the ejector and the reservoir through acoustic coupling medium 41.

Since the substrate well plate and the reservoir well plate are differently sized, there is only correspondence, not identity, between the movement of the ejector positioning means and the movement of the substrate well plate. Once properly aligned as shown in FIG. 2C, the acoustic radiation generator 35 of ejector 33 is activated to produce an acoustic wave that is then directed by focusing means 37 to a focal point near the fluid surface 19 from which droplet 53 is ejected onto the second well of the substrate well plate. It should be evident that such operation is illustrative of how the employed device may be used to transfer a plurality of fluids from one well plate to another of a different size. One of ordinary skill in the art will recognize that this type of transfer may be carried out even when both the ejector and substrate are in continuous motion. It should be further evident that a variety of combinations of reservoirs, well plates and/or substrates may be used in using the employed device to engage in fluid transfer. It should be still further evident that any reservoir may be filled with a fluid through acoustic ejection prior to deploying the reservoir for further fluid transfer, e.g., for array deposition. Additionally, the fluid in the reservoir may be synthesized in the reservoir, wherein the synthesis involves use of acoustic ejection fluid transfer in at least one synthesis step.

As discussed above, either individual, e.g., removable, reservoirs or well plates may be used to contain fluids that are to be ejected, wherein the reservoirs or the wells of the well plate are preferably substantially acoustically indistinguishable from one another. Also, unless it is intended that the ejector is to be submerged in the fluid to be ejected, the reservoirs or well plates must have acoustic transmission properties sufficient to allow acoustic radiation from the ejector to be conveyed to the surfaces of the fluids to be ejected. Typically, this involves providing reservoir or well bases that are sufficiently thin to allow acoustic radiation to travel therethrough without unacceptable dissipation. In addition, the material used in the construction of reservoirs must be compatible with the fluids contained therein. Thus, if it is intended that the reservoirs or wells contain an organic solvent such as acetonitrile, polymers that dissolve or swell in acetonitrile would be unsuitable for use in forming the reservoirs or well plates. For water-based fluids, a number of materials are suitable for the construction of reservoirs and include, but are not limited to, ceramics such as silicon oxide and aluminum oxide, metals such as stainless steel and platinum, and polymers such as polyester and polytetrafluoroethylene. Many well plates suitable for use with the employed device are commercially available and may contain, for example, 96, 384 or 1536 wells per well plate. Manufactures of suitable well plates for use in the employed device include Corning Inc. (Corning, N.Y.) and Greiner America, Inc. (Lake Mary, Fla.). However, the availability of such commercially available well plates does not preclude manufacture and use of custom-made well plates containing at least about 10,000 wells, or as many as 100,000 wells or more. For array forming applications, it is expected that about 100,000 to about 4,000,000 reservoirs may be employed. In addition, to reduce the amount of movement and time needed to align the ejector with each reservoir or reservoir well, it is preferable that the center of each reservoir is located not more than about 1 centimeter, preferably not more than about 1 millimeter and optimally not more than about 0.5 millimeter from a neighboring reservoir center.

Moreover, the device may be adapted to eject fluids of virtually any type and amount desired. The fluid may be aqueous and/or nonaqueous. Examples of fluids include, but are not limited to, aqueous fluids including water per se and water-solvated ionic and non-ionic solutions, organic solvents, and lipidic liquids, suspensions of immiscible fluids and suspensions or slurries of solids in liquids. Because the invention is readily adapted for use with high temperatures, fluids such as liquid metals, ceramic materials, and glasses may be used; see, e.g., co-pending patent application U.S. Ser. No. 09/669,194 ("Method and Apparatus for Generating Droplets of Immiscible Fluids"), inventors Ellson and Mutz, filed on Sep. 25, 2000, and assigned to Picoliter, Inc. (Mountain View, Calif.). U.S. Pat. Nos. 5,520,715 and 5,722,479 to Oeftering describe the use of acoustic ejection for liquid metal for forming structures using a single reservoir and adding fluid to maintain focus. U.S. Pat. No. 6,007,183 to Horine is another patent that pertains to the use of acoustic energy to eject droplets of liquid metal. The capability of producing fine droplets of such materials is in sharp contrast to piezoelectric technology, insofar as piezoelectric systems perform suboptimally at elevated temperatures. Furthermore, because of the precision that is possible using the inventive technology, the device may be used to eject droplets from a reservoir adapted to contain no more than about 100 nanoliters of fluid, preferably no more than 10 nanoliters of fluid. In certain cases, the ejector may be adapted to eject a droplet from a reservoir adapted to contain about 1 to about 100 nanoliters of fluid. This is particularly useful when the fluid to be ejected contains rare or expensive biomolecules, wherein it may be desirable to eject droplets having a volume of about up to 1 picoliter.

It will be appreciated that various components of the device may require individual control or synchronization to form an array on a substrate. For example, the ejector positioning means may be adapted to eject droplets from each reservoir in a predetermined sequence associated with an array to be prepared on a substrate surface. Similarly, the substrate positioning means for positioning the substrate surface with respect to the ejector may be adapted to position the substrate surface to receive droplets in a pattern or array thereon. Either or both positioning means, i.e., the ejector positioning means and the substrate positioning means, may be constructed from, for example, motors, levers, pulleys, gears, a combination thereof, or other electromechanical or mechanical means known to one of ordinary skill in the art. It is preferable to ensure that there is a correspondence between the movement of the substrate, the movement of the ejector and the activation of the ejector to ensure proper array formation.

The device may also include certain performance-enhancing features. For example, the device may include a cooling means for lowering the temperature of the substrate surface to ensure, for example, that the ejected droplets adhere to the substrate. The cooling means may be adapted to maintain the substrate surface at a temperature that allows fluid to partially or preferably substantially solidify after the fluid comes into contact therewith. In the case of aqueous fluids, the cooling means should have the capacity to maintain the substrate surface at about 0° C. In addition, repeated application of acoustic energy to a reservoir of fluid may result in heating of the fluid. Heating can of course result in unwanted changes in fluid properties such as viscosity, surface tension and density. Thus, the device may further comprise means for maintaining fluid in the reservoirs at a constant temperature. Design and construction of such temperature maintaining means are known to one of ordinary skill in the art and may comprise, e.g., components such a heating element, a cooling element, or a combination thereof. For many biomolecular deposition applications, it is generally desired that the fluid containing the biomolecule is kept at a constant temperature without deviating more than about 1° C. or 2° C. therefrom. In addition, for a biomolecular fluid that is particularly heat sensitive, it is preferred that the fluid be kept at a temperature that does not exceed about 10° C. above the melting point of the fluid, preferably at a temperature that does not exceed about 5° C. above the melting point of the fluid. Thus, for example, when the biomolecule-containing fluid is aqueous, it may be optimal to keep the fluid at about 4° C. during ejection.

Alternatively for some applications, especially those involving acoustic deposition of molten metals or other materials, a heating element may be provided for maintaining the substrate at a temperature below the melting point of the molten material, but above ambient temperature so that control of the rapidity of cooling may be effected. The rapidity of cooling may thus be controlled, to permit experimentation regarding the properties of combinatorial compositions such as molten deposited alloys cooled at different temperatures. For example, it is known that metastable materials are generally more likely to be formed with rapid cooling, and other strongly irreversible conditions. The approach of generating materials by different cooling or quenching rates my be termed combinatorial quenching, and could be effected by changing the substrate temperature between acoustic ejections of the molten material. A more convenient method of evaluating combinatorial compositions solidified from the molten state at different rates is by generating multiple arrays having the same pattern of nominal compositions ejected acoustically in the molten state onto substrates maintained at different temperatures.

For example, an iron carbon composition array could be ejected onto an appropriate substrate such as aluminum oxide, a ceramic, monocrystalline Si or monocrystalline Si upon which crystalline tetrahedral carbon (diamond) has been grown by routine methods. Arrays having the same pattern of nominal compositions may be spotted under identical conditions except that the substrate is maintained at a different temperature for each, and the resulting material properties may be compared for the differently quenched compositions.

In some cases, a substrate surface may be modified prior to formation of an array thereon. Surface modification may involve functionalization or defunctionalization, smoothing or roughening, changing surface conductivity, coating, degradation, passivation or otherwise altering the surface's chemical composition or physical properties. A preferred surface modification method involves altering the wetting properties of the surface, for example to facilitate confinement of a droplet ejected on the surface within a designated area or enhancement of the kinetics for the surface attachment of molecular moieties contained in the ejected droplet. A preferred method for altering the wetting properties of the substrate surface involves deposition of droplets of a suitable surface modification fluid at each designated site of the substrate surface prior to acoustic ejection of fluids to form an array thereon. In this way, the "spread" of the acoustically ejected droplets may be optimized and consistency in spot size (i.e., diameter, height and overall shape) ensured. One way to implement the method involves acoustically coupling the ejector to a modifier reservoir containing a surface modification fluid and then activating the ejector, as described in detail above, to produce and eject a droplet of surface modification fluid toward a designated site on the substrate surface. The method is repeated as desired to deposit surface modification fluid at additional designated sites. This method is useful in a number of applications including, but not limited to, spotting oligomers to form an array on a substrate surface or synthesizing array oligomers in situ. As noted above, other physical properties of the surface that may be modified include thermal properties and electrical conductivity.

FIG. 3 schematically illustrates in simplified cross-sectional view a specific embodiment of the aforementioned method in which a dimer is synthesized on a substrate using a device similar to that illustrated in FIG. 1, but including a modifier reservoir 59 containing a surface modification fluid 60 having a fluid surface 61. FIG. 3A illustrates the ejection of a droplet 63 of surface modification fluid 60 selected to alter the wetting properties of a designated site on surface 51 of the substrate 45 where the dimer is to be synthesized. The ejector 33 is positioned by the ejector positioning means 43 below modifier reservoir 59 in order to achieve acoustic coupling therewith through acoustic coupling medium 41. Substrate 45 is positioned above the modifier reservoir 19 at a location that enables acoustic deposition of a droplet of surface modification fluid 60 at a designated site. Once the ejector 33, the modifier reservoir 59 and the substrate 45 are in proper alignment, the acoustic radiation generator 35 is activated to produce acoustic radiation that is directed by the focusing means 37 in a manner that enables ejection of droplet 63 of the surface modification fluid 60 from the fluid surface 61 onto a designated site on the underside surface 51 of the substrate. Once the droplet 63 contacts the substrate surface 51, the droplet modifies an area of the substrate surface to result in an increase or decrease in the surface energy of the area with respect to deposited fluids.

Figure 3A:
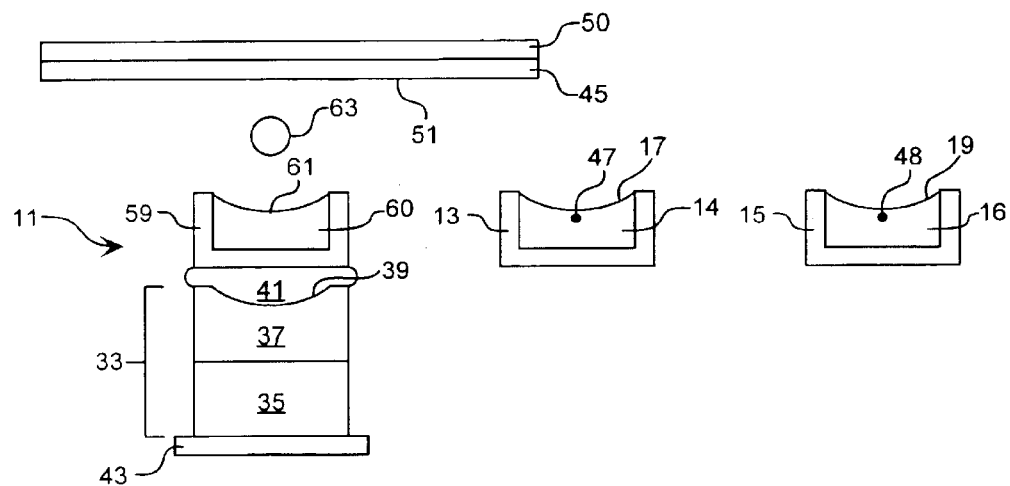
FIGS. 3A, 3B, 3C, and 3D, collectively referred to as FIG. 3, schematically illustrate in simplified cross-sectional view an embodiment of the inventive method in which a dimer is synthesized in situ on a substrate using the device of FIG. 1.
Figure 3B:
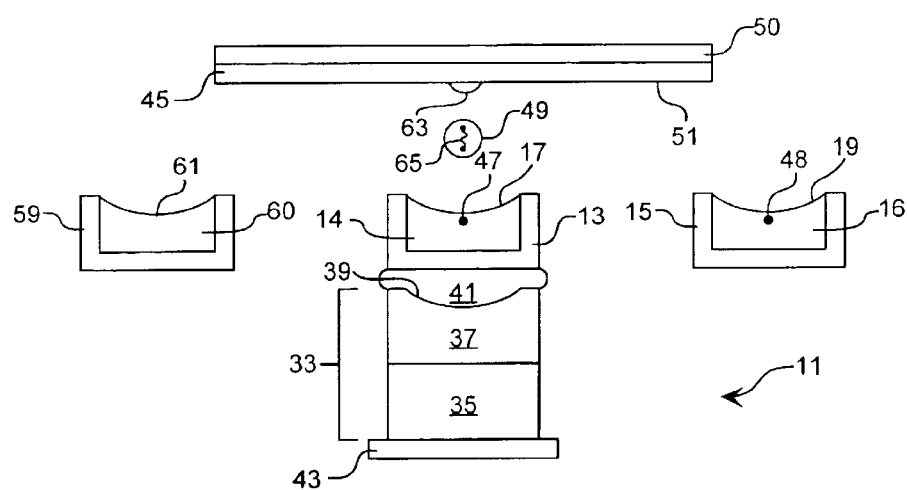

Then, as shown in FIG. 3B, the substrate 45 is repositioned by the substrate positioning means 50 such that the region of the substrate surface modified by droplet 63 is located directly over reservoir 13. FIG. 3B also shows that the ejector 33 is positioned by the ejector positioning means below reservoir 13 to acoustically couple the ejector and the reservoir through acoustic coupling medium 41. Once properly aligned, the ejector 33 is again activated so as to eject droplet 49 onto substrate. Droplet 49 contains a first monomeric moiety 65, preferably a biomolecule such as a protected nucleoside or amino acid, which after contact with the substrate surface attaches thereto by covalent bonding or adsorption.

Figure 3C:
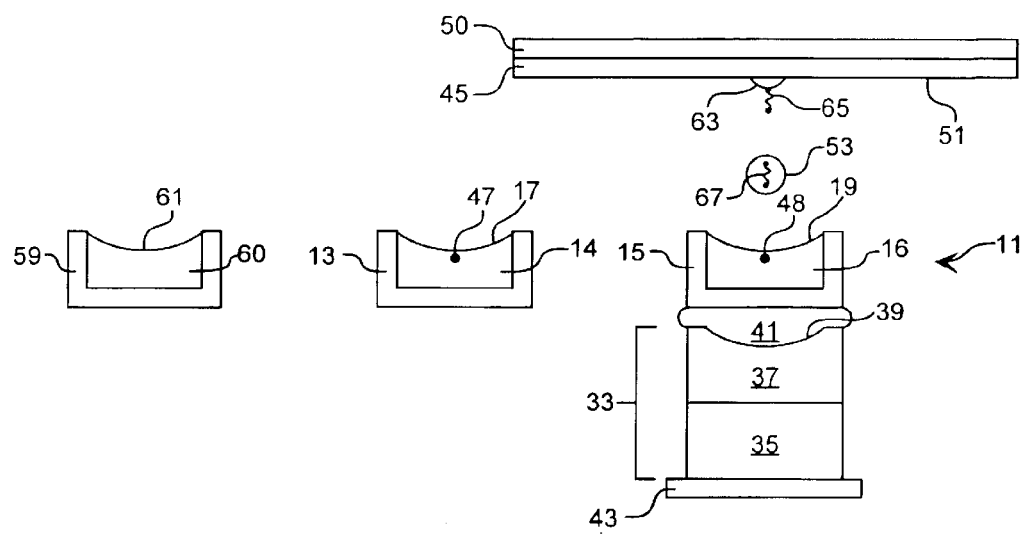
Figure 3D:
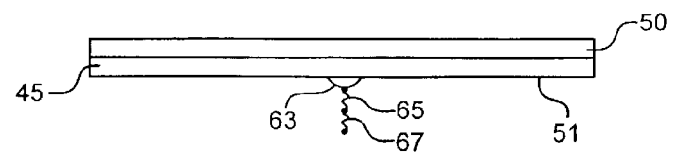

Then, as shown in FIG. 3C, the substrate 45 is again repositioned by the substrate positioning means 50 such that the site having the first monomeric moiety 65 attached thereto is located directly over reservoir 15 in order to receive a droplet therefrom. FIG. 3B also shows that the ejector 33 is positioned by the ejector positioning means below reservoir 15 to acoustically couple the ejector and the reservoir through acoustic coupling medium 41. Once properly aligned, the ejector 33 is again activated so as to eject droplet 53 is ejected onto substrate. Droplet 53 contains a second monomeric moiety 67, adapted for attachment to the first monomeric moiety 65, typically involving formation of a covalent bond so as to generate a dimer as illustrated in FIG. 3D. The aforementioned steps may be repeated to generate an oligomer, e.g., an oligonucleotide, of a desired length.

The chemistry employed in synthesizing substrate-bound oligomers will generally involve conventional techniques known to those skilled in the art of organic and biochemistry and/or described in the pertinent literature and texts.

Alternatively, an oligomer may be synthesized prior to attachment to the substrate surface and then "spotted" onto a particular locus on the surface using the methodology of the invention as described in detail above. Again, the oligomer may be an oligonucleotide, an oligopeptide, or any other biomolecular (or nonbiomolecular) oligomer moiety. Preparation of substrate-bound peptidic molecules, e.g., in the formation of peptide arrays and protein arrays, is described in co-pending patent application U.S. Ser. No. 09/669,997 ("Focused Acoustic Energy in the Preparation of Peptidic Arrays"), inventors Mutz and Ellson, filed Sep. 25, 2000 and assigned to Picoliter, Inc. (Mountain View, Calif.). Preparation of substrate-bound oligonucleotides, particularly arrays of oligonucleotides wherein at least one of the oligonucleotides contains partially nonhybridizing segments, is described in co-pending patent application U.S. Ser. No. 09/669,267 ("Arrays of Oligonucleotides Containing Nonhybridizing Segments"), inventor Ellson, also filed on Sep. 25, 2000 and assigned to Picoliter, Inc. (Cupertino, Calif.).

It should be evident, then, that many variations of the invention are possible. For example, each of the ejected droplets may be deposited as an isolated and "final" feature, e.g., in spotting oligonucleotides, as mentioned above. Alternatively, or in addition, a plurality of ejected droplets may be deposited on the same location of a substrate surface in order to synthesize a biomolecular array in situ, as described above. For array fabrication, it is expected that various washing steps may be used between droplet ejection steps. Such wash steps may involve, e.g., submerging the entire substrate surface on which features have been deposited in a washing fluid. In a modification of this process, the substrate surface may be deposited on a fluid containing a reagent that chemically alters all features at substantially the same time, e.g., to activate and/or deprotect biomolecular features already deposited on the substrate surface to provide sites on which additional coupling reactions may occur.

The aforementioned focused acoustic energy system enables ejection of droplets at a rate of at least about 1,000,000 droplets per minute from the same reservoir, and at a rate of at least about 100,000 drops per minute from different reservoirs. In addition, current positioning technology allows for the ejector positioning means to move from one reservoir to another quickly and in a controlled manner, thereby allowing fast and controlled ejection of different fluids. That is, current commercially available technology allows the ejector to be moved from one reservoir to another, with repeatable and controlled acoustic coupling at each reservoir, in less than about 0.1 second for high performance positioning means and in less than about 1 second for ordinary positioning means. A custom designed system will allow the ejector to be moved from one reservoir to another with repeatable and controlled acoustic coupling in less than about 0.001 second. In order to provide a custom designed system, it is important to keep in mind that there are two basic kinds of motion: pulse and continuous. Pulse motion involves the discrete steps of moving an ejector into position, emitting acoustic energy, and moving the ejector to the next position; again, using a high performance positioning means with such a method allows repeatable and controlled acoustic coupling at each reservoir in less than 0.1 second. A continuous motion design, on the other hand, moves the ejector and the reservoirs continuously, although not at the same speed, and provides for ejection during movement. Since the pulse width is very short, this type of process enables over 10 Hz reservoir transitions, and even over 1000 Hz reservoir transitions.

In order to ensure the accuracy of fluid ejection, it is important to determine the location and the orientation of the fluid surface from which a droplet is to be ejected with respect to the ejector. Otherwise, ejected droplets may be improperly sized or travel in an improper trajectory. Thus, another embodiment of the invention relates to a method for determining the height of a fluid surface in a reservoir between ejection events. The method involves acoustically coupling a fluid-containing reservoir to an acoustic radiation generator and activating the generator to produce a detection acoustic wave that travels to the fluid surface and is reflected thereby as a reflected acoustic wave. Parameters of the reflected acoustic radiation are then analyzed in order to assess the spatial relationship between the acoustic radiation generator and the fluid surface. Such an analysis will involve the determination of the distance between the acoustic radiation generator and the fluid surface and/or the orientation of the fluid surface in relationship to the acoustic radiation generator.

More particularly, the acoustic radiation generator may be activated so as to generate low energy acoustic radiation that is insufficiently energetic to eject a droplet from the fluid surface. This is typically done by using an extremely short pulse (on the order of tens of nanoseconds) relative to that normally required for droplet ejection (on the order of microseconds). By determining the time it takes for the acoustic radiation to be reflected by the fluid surface back to the acoustic radiation generator and then correlating that time with the speed of sound in the fluid, the distance B and thus the fluid height—may be calculated. Of course, care must be taken in order to ensure that acoustic radiation reflected by the interface between the reservoir base and the fluid is discounted. It will be appreciated by those of ordinary skill in the art of acoustic microscopy that such a method employs conventional or modified sonar techniques.

Once the analysis has been performed, an ejection acoustic wave having a focal point near the fluid surface is generated in order to eject at least one droplet of the fluid, wherein the optimum intensity and directionality of the ejection acoustic wave is determined using the aforementioned analysis optionally in combination with additional data. The "optimum" intensity and directionality are generally selected to produce droplets of consistent size and velocity. For example, the desired intensity and directionality of the ejection acoustic wave may be determined by using not only the spatial relationship assessed as above, but also geometric data associated with the reservoir, fluid property data associated with the fluid to be ejected, and/or by using historical droplet ejection data associated with the ejection sequence. In addition, the data may show the need to reposition the ejector so as to reposition the acoustic radiation generator with respect to the fluid surface, in order to ensure that the focal point of the ejection acoustic wave is near the fluid surface, where desired. For example, if analysis reveals that the acoustic radiation generator is positioned such that the ejection acoustic wave cannot be focused near the fluid surface, the acoustic radiation generator is repositioned using vertical, horizontal and/or rotational movement to allow appropriate focusing of the ejection acoustic wave.

In general, screening for the properties of the array constituents will be performed in a manner appropriate to the combinatorial array. Screening for biological properties such as ligand binding or hybridization may be generally performed in the manner described in U.S. Pat. Nos. 5,744,305 and 5,445,934 to Fodor et al. U.S. Pat. Nos. 5,143,854 and 5,405,783 to Pirrung et al., and U.S. Pat. Nos. 5,700,637 and 6,054,270 to Southern et al.

Screening for material properties may be effected by measuring physical and chemical properties, including by way of example rather than limitation, measuring the chemical, mechanical, optical, thermal, electrical or electronic, by routine methods easily adaptable to microarrays. In addition to bulk material characteristics or properties, surface specific properties may be measured by surface specific physical techniques and physical techniques that are adapted to surface characterization. Macroscopic surface phenomena including adsorption, catalysis, surface reactions including oxidation, hardness, lubrication and friction, may be examined on a molecular scale using such characterization techniques. Various physical surface characterization techniques include without limitation diffractive techniques, spectroscopic techniques, microscopic surface imaging techniques, surface ionization mass spectroscopic techniques, thermal desorption techniques and ellipsometry. It should be appreciated that these classifications are arbitrary made for purposes of explication, and some overlap may exist.

In addition to bulk material characteristics or properties, surface specific properties may be measured by surface specific physical techniques and physical techniques that are adapted to surface characterization. Macroscopic surface phenomena including adsorption, catalysis, surface reactions including oxidation, hardness, lubrication and friction, may be examined on a molecular scale using such characterization techniques. Various physical surface characterization techniques include without limitation diffractive techniques, spectroscopic techniques, microscopic surface imaging techniques, surface ionization mass spectroscopic techniques, thermal desorption techniques and ellipsometry. It should be appreciated that these classifications are arbitrary made for purposes of explication, and some overlap may exist.

In addition to bulk material characteristics or properties, surface specific properties may be measured by surface specific physical techniques and physical techniques that are adapted to surface characterization. Macroscopic surface phenomena including adsorption, catalysis, surface reactions including oxidation, hardness, lubrication and friction, may be examined on a molecular scale using such characterization techniques. Various physical surface characterization techniques include without limitation diffractive techniques, spectroscopic techniques, microscopic surface imaging techniques, surface ionization mass spectroscopic techniques, thermal desorption techniques and ellipsometry. It should be appreciated that these classifications are arbitrary made for purposes of explication, and some overlap may exist.

Diffractive techniques include X-ray diffraction (XRD, extreme glancing angle for surface), high, medium and low energy electron diffraction (HEED, MEED, LEED), reflection HEED (RHEED), spin-polarized LEED (SPLEED, especially useful in characterizing surface magnetism and magnetic ordering) low energy positron diffraction (LEPD), normal photoelectron diffraction (NPD), atomic or He diffraction (AD) and adaptation of neutron diffraction for surface sensitivity. Angle resolved X-ray photoelectron diffraction (ARXPD) measures angular photoemission from X-ray photoelectron excitation and is therefore more akin to a spectroscopic technique.

Spectroscopic techniques utilizing electron excitation include Auger electron spectroscopy (AES) which detects 2° electrons ejected by decay of atoms to ground state after core hole electronic excitation and related techniques, including Auger electron appearance potential spectroscopy (AEAPS), angle resolved AES (ARAES), electron appearance potential fine structure spectroscopy (EAPFS), disappearance potential spectroscopy (DAPS). Additional spectroscopic techniques employing electron beam excitation include conversion electron Mossbauer spectroscopy (CEM), electron-stimulated ion angular distribution (ESIAD), electron energy loss spectroscopy (EELS) and high resolution EELS (HREELS), and related techniques including electron energy near edge structured (ELNES), surface electron energy fine structure (SEELFS). An additional electron excitation based spectroscopic technique that measures modulation of the absorption cross section with energy 100–500 eV above the excitation threshold, often by measuring fluorescence as the core holes decay is extended X-ray energy loss fine structure (EXELFS), NPD APD. Inverse photoemission of electrons (IP) gives information on conduction bands and unoccupied orbitals.

Photon excitation-based spectroscopies that do not employ classical particles are exemplified by ultraviolet photoemission spectroscopy (UPS), X-ray photoemission spectroscopy (XPS, formerly known as ESCA, electron spectroscopy for chemical analysis). XPS related techniques include: photon-stimulated ion angular distribution (PSD) analogous to ESDIAD, appearance potential XPS (APXPS) in which the EAPFS cross section is monitored by fluorescence from decay of X-ray photoemitted core holes, various angle resolved photoemission techniques (ARPES) including, angle-resolved photoemission fine structure (ARPEFS), angle-resolved UV photoemission spectroscopy (ARUPS), angle-resolved XPS (ARXPS), ARXPD, near-edge X-ray absorption fine structure that uses energies approximately 30 eV above the excitation threshold to measure both primary photoemitted electrons and Auger electrons emitted by core hole decay (NEXAFS), extended X-ray absorption fine structure (EXAFS), surface EXAFS (SEXAFS) which measure primary photoemitted electrons (PE-SEXAFS) and Auger electrons emitted by core hole decay (Auger-SEXAFS) and ions emitted by photoelectrons (PSD-SEXAFS). Angle resolved X-ray photoemission spectroscopy (ARXPS) measures angular distribution of photoemitted electrons Infrared absorption spectroscopies that provide molecular structure information on adsorbate, adsorbed molecules, include infrared reflection absorption spectroscopy (IRAS). Deconvolution of broad band IRAS using a Doppler shifted source and Fourier analysis is termed Fourier transform IR (FTIR). These techniques are especially important in determining identity and conformation of adsorbed atoms and molecules for predicting potential catalytic properties, e.g. for identifying which composition in an array should be further tested for catalytic properties. Most catalytic mechanisms proceed from adsorption, including physi- and chemisorption or both (Somorjai, *Introduction to Surface Chemistry and Catalysis* (1994) John Wiley & Sons).

Scattering based techniques include Rutherford back scattering (RBS), ion scattering spectroscopy (ISS), high energy ion scattering spectroscopy (HEIS) mid-energy ion scattering spectroscopy MEIS low energy ion scattering spectroscopy (LEIS) Microscopic techniques include scanning tunneling microscopy (STM) and applied force microscopy (AFM), which can detect adsorbed molecules. For example, STM has been used to demonstrate resident adsorbate as well as other surface contours, for example the liquid crystal molecule 5-nonyl-2-nonoxylphenylpyrimidine adsorbed on a graphite surface Foster et al (1988) *Nature* 338:137). AFM detects a deflection in a cantilever caused by surface contact, and includes scanning force microscopy (SFM) and friction force microscopy (FFM); force based macroscopic techniques can be used to study non-conductive surfaces, as they do not require electron tunneling from the bulk Mass spectroscopic (MS) techniques include SIMS and MALDI-MS, which can be used to obtain information on ionized macromolecules including biomacromolecules either formed on the substrate combinatorially or adsorbing to a surface of a combinatorial material. U.S. Pat. No. 5,959,297 describes scanning mass spectrometer having an ionization chamber and a collector that outputs an electrical signal responsive to the quantity of gas ions contacting the collector surface and methods for screening arrayed libraries of different materials that have been exposed in parallel to a gas reactant. MS techniques are also combinable with molecular beam (MB) techniques, especially molecular beam reactive scattering (MBRS), to permit detection of adsorption, and residence time at the adsorbate site, reactions, including surface catalysis of reactions of adsorbed molecules, and the angular distribution of adsorbate, and any product of reaction ejected from the surface (Atkins, *Physical Chemistry*, $6^{th}$ Ed. (1998) W. H. Freeman & Co., N.Y.). MS probing of microarrayed sites exposed to reactants by acoustic delivery can be combined with micro-desorptive MB techniques, or any of the techniques described herein which sample a surface area having sufficiently small dimensions. For example, micro-FTIR can be performed to adequate resolution with a sample diameter of 5 μm. A list of techniques and their associated sample diameter follows: XPS—10 μm; MALDI-MS—10 μm; SIMS—1 μm (surface imaging), 30 μm (depth profiling); AES—0.1 μm (100 nm); FE-AES—<15 nm; AFM/STM—1.5–5 nm; SEM 4.5 nm; FE-SEM—1.5 nm; RBS—2 mm; MB-MS—0.1–0.3 mm. It will be appreciated that the array can be designed for the characterization technique, for example in non-biomacromolecular arrays where tested samples are not as rare and techniques involving larger sampling areas, such as SIMS depth profiling are desired sites having dimensions on the order of 100 μm may be used, corresponding to a density of about 10,000 sites/cm². Measurements of such properties as conductivity are further facilitated by larger features.

The thermal pattern of an array may be captured by an infrared camera to reveal hot spots such as catalytic regions, reacting regions and regions of adsorption in an array of materials. For example, a parallel screening method based on reaction heat absorbed from a surface catalytic reaction has been reported (Moates et al. (1996) *Ind. Eng. Chem. Res.* 35:4801–03). In the surface catalyzed oxidation of hydrogen over a metallic surface, IR radiation images of an array of potential catalysts reveal the active catalysts. The hot spots in the image, corresponding to array sites having catalytic activity, can be resolved by an infrared camera. Despite deviations in the heat capacity and surface thermal conductivity between materials creating the possibility that array sites having similar catalytic activity may rise in temperature to different extents, the presence or absence of detectable heating is a semiquantitative indication of the enthalpic release sufficient for screening to identify materials having some catalytic activity. Analogously for adsorption, even if the heat of adsorption for a given molecule can depend on the adsorption site and different materials can have different adsorption sites for the same molecule, heating of the array site is adequate for screening material having surfaces that adsorb a given molecule for various purposes including potential catalysis of reactions involving that molecule. The spontaneous reaction, as by surface rearrangement, oxidation or other process may also be detectable by detection of surface heating. As surfaces are inherently metastable and the relative metastability of the surface often determines the usefulness of a material as determining the useful life of a manufacture from the material, determining the surface reactivity under various conditions is important. Physical, chemical, biological and/or biomaterials/biocompatibility measurement of the kinetics of surface rearrangement generally and specific mechanistic included processes versus temperature will yield valuable information on free energy of activation of various processes. Infrared imaging also may be useful for such determinations, but because many if not most spontaneous surface phenomena are likely to be entropic phenomena, reliance must not be placed solely upon semiquantitative thermodynamic measurements.

Biomaterial properties may also be characterized or screened. In some cases, arrays may be implanted into laboratory animals, and fibrosis, inflammatory changes, promotion of protein aggregation and the like can be compared for the naked substrate and various nearby combinatorial sites, although ultimately individual materials should be implanted separately. In vitro approaches to biocompatibility include measuring adsorption of various proteins and mixtures thereof over time at the different sites. Surfaces that (1) exhibit low levels of (2) saturable adsorption for (3) the fewest different proteins and (4) do not denature the adsorbate proteins are most likely to be biocompatible. For example, polyethylene glycol (PEG) modified Si surfaces, in which the amount of adsorbate over time saturates at relatively low levels, were shown to be more biocompatible than unmodified surface, which continues to accumulate adsorbate over all observed time periods (Zhang et al (1998) *Biomaterials* 19(10):953–60). Zhang et al. study adsorption of albumin, fibrinogen, and IgG to Si surfaces having self assembled PEG by ellipsometry to evaluate the non-fouling and non-immunogenic properties of the surfaces; additionally, adhesion and proliferation of human fibroblast and Hela cells onto the modified surfaces were investigated to examine their tissue biocompatibility. Adsorption experiments on polymer functionalized surfaces suggest entropic effect, evidenced by conformationally more labile polymer having greater anti-adsorption effect (Cordova et al. (1997) *Anal. Chem.* 69(7):1370–9) that may effect saturation by preventing denaturation and layering non-specific aggregation.

Suitable analytical techniques for analyzing combinatorial libraries prepared herein are set forth in the following table.

| ANALYTICAL TECHNIQUE | TYPICAL USE | SIGNAL DETECTED | ELEMENTS DETECTED | ORGANIC DATA | DETECTION LIMITS | DEPTH RESOLUTION | IMAGE OR MAP | LATERAL RESOLUTION |
|---|---|---|---|---|---|---|---|---|
| AES | Surface analysis and high resolution depth profiling | Auger electrons from near-surface atoms | Li—U | — | 0.1–1 atom % | <2 nm | Y | 100 nm |
| FE AES | Surface analysis, micro-analysis, and micro-area depth profiling | Auger electrons from near-surface atoms | Li—U | — | 0.1–1 atom % | 2–6 nm | Y | <15 nm |
| AFM STM | Surface imaging with near atomic resolution | Atomic scale surface contour | — | — | — | 0.01 nm | Y | 1.5–5 nm |
| micro-FTIR | Identification; polymers, organic films, fibers, and liquids | infrared absorption | — | chemical bonds and groups | 0.1–100 ppm | — | N | 5 μM |
| TXRF | Metal presence on surface | fluorescent X-rays | S—U | — | $1 \times 10^9$– $1 \times 10^{12}$ atoms/cm² | — | Y | 10 mm |
| XPS ESCA | Surface analysis: organic and inorganic molecules | photo-e⁻ | Li—U | — | 0.1–1 atom % | 1–10 nm | Y | 10 μM to 2 mm |
| HFS | Quantitative H in thin film | scattered H atoms | H, D | — | 0.1 atom % | 50 nm | N | 2 mm × 10 mm |

-continued

| ANALYTICAL TECHNIQUE | TYPICAL USE | SIGNAL DETECTED | ELEMENTS DETECTED | ORGANIC DATA | DETECTION LIMITS | DEPTH RESOLUTION | IMAGE OR MAP | LATERAL RESOLUTION |
|---|---|---|---|---|---|---|---|---|
| RBS | Quantitative thin film composition and thickness | back-scattered He atoms | Li—U | — | 1–10 (Z < 20); 0.01–1 (20 < Z < 70); 0.001–0.01 (Z > 70); (atom %) | 2–20 nm | Y | 2 mm |
| SEM EDS | Imaging and elemental micro-analysis | secondary and back-scattered electrons and X-rays | B—U | — | 0.1–1 atom % | 1–5 $\mu$M (EDS) | Y | 4.5 nm (SEM); 1 $\mu$M (EDS) |
| Quad SIMS | Dopant & impurity depth profiling, surface micro-analysis | secondary ions | H—U | — | $1 \times 10^{14}$– $1 \times 10^{17}$ atoms/cm$^3$ | <5 nm | Y | <5 $\mu$M (imaging); 30 $\mu$M (depth profiling) |
| TOF SIMS | Surface micro-analysis: organics, plastics & polymers | secondary ions, atoms and molecules | H—U | Molecular ions to mass $1 \times 10^4$ | <1 ppma, $1 \times 10^8$ atom/cm$^2$ | 1 mono-layer | Y | 0.10 $\mu$M |
| MALDI | Protein, peptide, & polymer MW distr. | Large molecular ions | — | Molecular ions to mass $1.5 \times 10^5$ | femtomole-picomole | — | N | 10 $\mu$M |
| FE SEM | High resolution imaging of polished surface | secondary and back-scattered electrons | — | — | — | — | Y | 1.5 nm |
| FE SEM (in lens) | Ultra-high res. imaging w. contrast medium | secondary and back-scattered electrons | — | — | — | — | Y | 0.7 nm |
| SIMS | Dopant and impurity depth profiling, surface micro-analysis | secondary electrons | H—U | — | $1 \times 10^{12}$– $1 \times 10^{16}$ atoms/cm$^3$ (ppb–ppm) | 5–30 nm | Y | 1 $\mu$M (imaging); 30 $\mu$M (depth profiling) |

In general, with respect to the screening of arrayed materials for various properties, those surface physical characterization techniques capable of generating a map of the surface microstructures of arrayed materials are of use in identifying various potential properties of the surface, especially physical properties of the surface pertinent to the material properties, including surface roughness and grain orientation, and functionalization, including, for example, silanol formation and electron cloud orientation in crystalline silicon surfaces, and potential chemical and physical adsorption (chemi-, physi-sorption) sites for various molecules, information that may be useful of itself and in predicting potential for catalytic activity. The ordinarily skilled in combinatorial chemistry will appreciate that the methods of the instant invention are applicable to all manner of crystallizations. Organic and inorganic compounds may be crystallized by the combinatorial experimental methods of acoustic droplet deposition. Such crystallization may occur from aqueous or other solutions, or from melts. Such crystallizations may be by spontaneous nucleation or from nucleation by addition of seed crystals. Seed crystals suspended in fluid can be added to the combinatorial droplet preparations deposited by acoustic deposition. The methods of the invention can thus readily be applied by one of ordinary skill to determining conditions ideal for crystallizing anything from, e.g., diamonds to glucose crystals. The instant invention also will readily be appreciated to be applicable to determining conditions that do not favor crystallization, but instead favor the formation of a glass or another amorphous phase. Additionally, the small volume combinatorial experimental methods of the instant invention may be employed to determine conditions that favor one form of crystallization over another (e.g., a particular polymorph; a polycrystalline aggregate rather than a small number of single crystals; a particular morphology, such as fibrous, tabular, or equant crystals; or a particular density of defects).

Figure 4A:
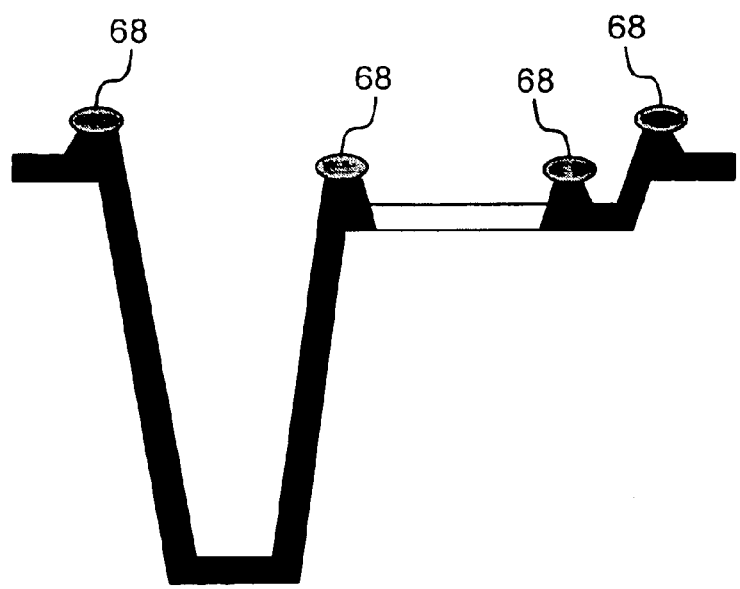
FIGS. 4A, 4B, and 4C, collectively referred to as FIG. 4, depict different conventionally sized reservoir and protein crystallization setups.
Figure 4B:
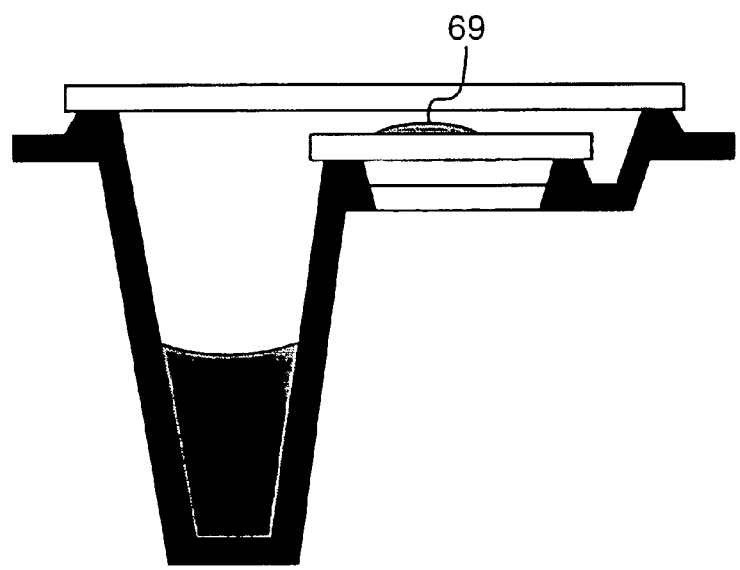
Figure 4C:
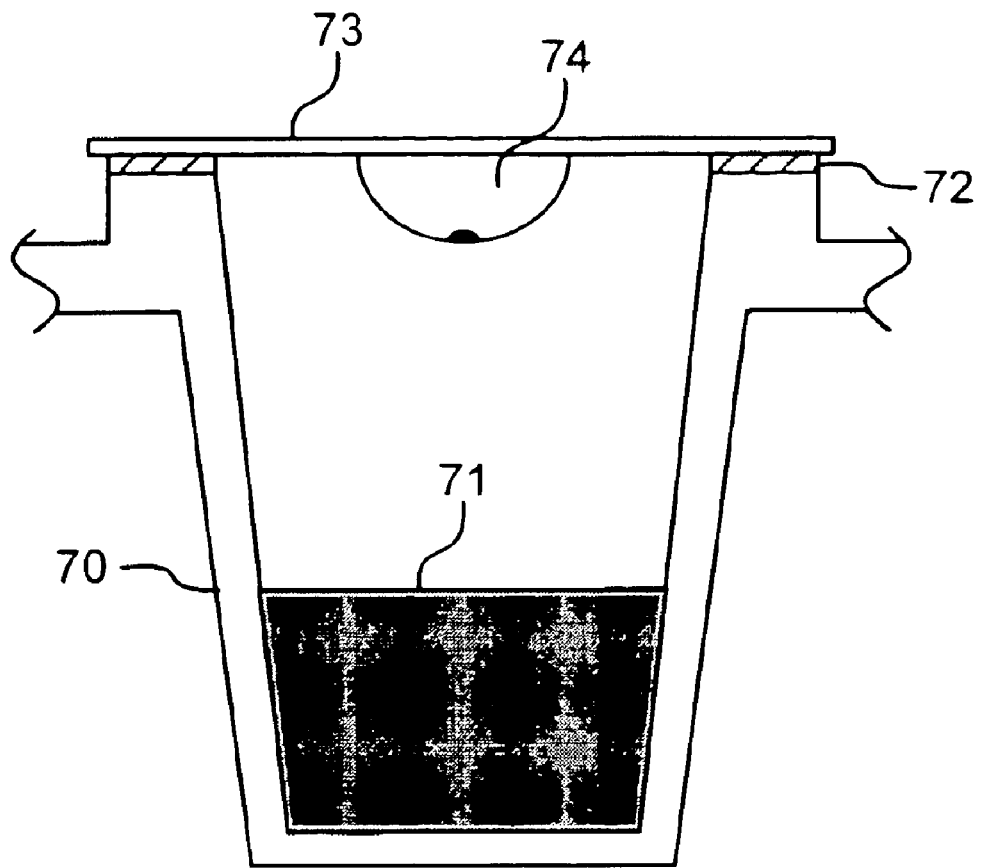

Acoustic drop ejection (ADE) also provides a method for increasing the number of crystallization conditions assayed for a given quantity of a macromolecule, such as a protein or nucleic acid. Current high-throughput methods are able to screen nanodroplets (volumes as small as 40 nL). The hundred-fold reduction of experimental crystallization volume to 40 nL from to 4 $\mu$L (used in conventional methods) conserves protein supplies, allows the screening of about 480 different crystallization conditions per protein per hour, and reduces the time required for crystallization from several days to several hours (Stevens (2000), *Curr. Opin. Struct. Biol.* 10:558). The use of smaller volumes decreases diffusion time, thus increasing rapidity of both nucleation and crystal formation, and can also accelerate crystallization due to faster rates of vapor diffusion than those in the commonly used standing drop (FIG. 4A, FIG. 4B) and hanging drop (FIG. 4B) techniques. In these methods, the drop is placed in a small container sealed to the outside atmosphere, in the presence of a reservoir, 70 (FIG. 4C), containing a solvent solution, 71 (FIG. 4C), that resembles the composition of the solvating liquid of the biomacromolecule or moiety in the experimental droplet without containing the biomacromolecule or other moiety of interest for crystallization. A gasket or other seal is employed to seal off the container from the atmosphere, 68 (FIG. 4A), 72 (FIG. 4C). Often the gasket material is a grease such as high-vacuum grease.

Usually the solvent solution contained in the reservoir is slightly hypertonic relative to the fluid in the experimental droplet, permitting solvent diffusion out of the droplet in a manner that favors orderly crystal growth. The artisan of ordinary skill will immediately appreciate that a slightly hypotonic reservoir solution may be sometimes desirable. For example it is known that protein nucleation often requires a high concentration of the protein of interest for crystallization, while the best quality crystals for crystallographic structure determination are typically grown at lower concentrations (McRee, *Practical Protein Crystallography*, $2^{nd}$ Ed. Academic Press, 1999). Thus the reservoir solution might contain a less hypertonic or perhaps even slightly hypotonic solution after nucleation has occurred.

Multiple drop experiments are performed using standard sized crystallization setups of the type depicted in FIG. 4. Acoustic ejection can form an array of hanging droplets, each with a volume of picoliters, at densities of 1,000/cm$^2$, 10,000/cm$^2$, or greater, allowing several thousand experiments to be performed with the same amount of material that would be used to perform one standard hanging drop experiment. This permits duplication as well as combinatorial experimentation with small amounts of biomacromolecule. The hanging drops can be generated without the need for inverting the cover slip after depositing the fluid on it. Further, dilution can be obtained by acoustically ejecting reservoir fluid onto overlying hanging droplets without breaking the gasket seal. The initial preparation of the experiment commonly requires reservoir fluid to be deposited onto a droplet containing the protein, and this must be done rapidly to prevent overdessication from the atmosphere. ADE permits the dilution to be performed after sealing the gasket. Standard-size sitting droplet containers can also be adapted for use with dense arrays of picoliter volumes on each cover slip. Clearly, current advances in microfabrication techniques permit the production of individual microwell arrays for hanging or sitting experiments involving picoliter-size droplets. The atomically smooth surfaces obtainable by microfabrication of monocrystalline Si and the like reduce the amount of sealing required, and may obviate the need for a separate gasket. Alternatively, patterned polymers, including photolabile polymers routinely used in the microelectronics industry, can be employed as gaskets for microfabricated well arrays. Individual droplets or multiple droplets comprising crystallization experiments may be placed in the individual microwells.

The solvent reservoir may be manipulated quickly. Fluid in standard sized reservoirs for crystallization experiments (for example, the round cover slip used in the conventionally sized hanging drop container depicted in FIG. 4C is 18–22 mm in diameter) may be manipulated by conventional methods such as micropipetting, or by acoustic deposition into, and ejection from, the reservoir. If the reservoirs are significantly smaller, for example in a microfabricated array of individual picoliter volume hanging droplets, the fluid in the microwells can conveniently and effectively be titrated to the desired composition by acoustic deposition and ejection, thus obviating the need to provide microfluidic channels and the like. Microfluidic channels increase the complexity of the microfabrication, and are incapable of accurately and precisely delivering or removing the small volumes to the reservoirs that may be effected by acoustic deposition/ejection.

By using ADE to dispense volumes ranging from 0.1 picoliter to several nanoliters, thereby scaling the volume of the experiments to the order of picoliters, the ability to form high-quality crystals in minutes as opposed to several hours becomes a reasonable expectation. Moreover, if the use of 40 nL volumes allows the screening of 480 conditions, the use of 40 pL volumes should allow the screening of at least 480,000 combinatorial conditions for a given supply of protein, or alternatively of the 480 conditions each repeated 1000 fold to capture stochastic nucleation events. Using volumes of about 40 pL will typically allow crystallization within several minutes.

The capability to accurately dispense volumes of such small magnitude immediately permits myriad combinatorial approaches. Stevens, (2000) supra, notes the importance of improvements in conventional microfluidics in the downscaling of protein crystallization experiments, observing that the solvent reservoir becomes unnecessary for some crystallizations when volumes are reduced from 4 mL to 40 nL. There exists, however, a significant possibility that downsizing to 40 pL may require a slightly hypotonic or isotonic reservoir to slow down the diffusion. Crystallographers often employ an oil-based coating on droplets to slow down diffusion out of the droplets (commonly referred to as a "microbatch" technique). The vapor diffusion method avoids applying oil to the experimental droplet, but caps the reservoir with an oil coating. These methods may be employed in down-scaled experiments by ADE, as will be described in more detail below.

Another oil-based method that could be adapted to preparation of a combinatorial crystallization array using picoliter-size droplet volumes is the "floating drop" method, described by Lorber et al. (1996) *Journal of Crystal Growth* 168:214–15. The standard-size floating drop technique employs two immiscible silicone oils having different densities in a well plate, allowing the crystallization experiment to float at the interface. A typical pair of such oils is poly-3,3,3-trifluoropropylmethylsiloxane (FMS), which is highly branched, dense, and viscous, and polydimethylsiloxane (DMS), which is unbranched, less dense, and less viscous. In conventional methods, the dispensation of FMS into standard 96 well plates is hindered by its high viscosity, but scaled down nozzleless acoustic deposition facilitates manipulation of the FMS. In the conventional method the DMS is deposited on top of the FMS, followed by the experimental fluid. For the scaled down version, microwells having dimensions of about 65 μm wide and deep and a capacity of about 250 pL are ideal. 100 pL of DMS is acoustically deposited in each well (open end down), and although runny, will be held in place by surface tension. The crystallization solution is then deposited as a droplet with volume of about 2 pL to 20 pL. If the total experimental fluid volume is towards the upper limit in volume, 20 pL, multiple droplet depositions may be used successfully, as individually deposited aqueous droplets will coalesce. Deposition of the experimental fluid is followed by deposition of 100 pL of FMS in each well, the viscous FMS sealing the experiment. Note that vapor diffusion occurs through the FMS, rather than through the DMS as in the standard floating drop experiment. This will typically be advantageous, as slower vapor diffusion usually produces superior crystals. Alternatively, the top of each well can be fashioned to communicate with the surrounding gas by sacrificial layer microfabrication methods described above. The array might also be inverted while at a slightly higher temperature than the ultimate experimental temperature, but this procedure may require larger wells, depending on the behavior of the FMS. Fluid reservoirs for solvent may also be provided by microfabrication.

Relatively dense arrays of small-volume droplets may be employed without any solvent reservoir. Such arrays may or may not require an oil coating to produce high-quality crystals suitable for high-resolution x-ray crystal structure analysis. These arrays should be isolated from the atmosphere, and if enclosed in a sufficiently small volume, the droplets that do not crystallize will serve as diffusion sinks for excess solvent in crystallizing droplets (the excess solvent due to solute depletion from crystallization). Alternatively, reservoirs may be easily microfabricated for droplet arrays, for example microchannels can surround a given number of arrayed droplets so that no droplet is greater than a desired distance from a fluid reservoir. More complicated microfabrication protocols may be employed to produce microwell reservoir droplet sites.

Acoustic technology can also be used to monitor the emergence and progression of protein crystallization: by scanning acoustically for nascent crystals, and then scanning periodically at those locales where such crystals were detected. At present, screening of crystal growth is performed with an optical microscope, commonly together with an image acquisition system. Optical screening, however, is often not adequate to discriminate between protein crystals and buffer crystals, because it does not supply information about composition. Buffer crystals tend to be denser and have lower water content than protein crystals. The generally weak intermolecular bonding of biomacromolecular crystals, relative to the covalent, metallic, or ionic bonds of most non-biomacromolecular crystals, leads to differences in mechanical properties. Acoustic waves are affected by the mechanical properties of the medium through which they propagate. Thus, acoustic waves are able to discern non-biomacromolecular from biomacromolecular crystals. Applying acoustic pulses to a solution of crystals and measuring resulting acoustic signals may consequently be employed to distinguish buffer crystals from protein crystals. Moreover, acoustic or sonic imaging methods (e.g., acoustic microscopy) are exquisitely sensitive to the size of any crystals imaged. Therefore, acoustic pulse technology can be used to assess the size and, more importantly, the composition of a growing crystal, without the need for cumbersome diffractometry procedures. Acoustic pulse technology can also be employed to study the kinetics of crystal nucleation and growth.

Once biomacromolecular crystals are made, they commonly must be kept cold during storage and during x-ray diffraction experiments. Focused acoustic energy may be conveniently used to manipulate crystals at low temperatures (e.g., at about 4° C. or lower) by forcing them to the surface and then ejecting them. Crystals may be ejected directly into closed-end capillaries or microcapillaries that can be mounted in a diffractometer. Smaller microcrystals, obtained from scaled down experiments that employ acoustic manipulation of reagent-containing picoliter droplets, may be mounted by acoustic deposition into microfabricated crystal mounts.

Crystal seeding can be implemented by ADE deposition of crystal fragments suspended in an appropriate fluid, often the mother liquor from which the seed crystals arose. Seeding by acoustic droplet ejection is applicable to many crystal-growing techniques, but is particularly useful in the crystallization of biomacromolecules as it conserves these generally scarce molecules. If crystals obtained from small volume experiments are not sufficiently large to yield high-resolution structures from the diffraction data, but are of otherwise sufficient quality, the experiments can be scaled up to volumes of the order of nanoliters, such as 40 nL, and the original crystals can be used to seed the scaled up experiments. Crystals obtained that are of insufficient quality can be redissolved for further crystallization attempts.

The methods of the present invention are useful for optimizing the crystallization of biopolymers and other biomacromolecules, particularly those biomacromolecules that have conformational structure, including, by way of example, proteins and various classes of RNAs. Conformational structure refers to levels of structure higher than primary structure or monomer sequence, including secondary, tertiary, and quaternary structures. Conformation is widely appreciated to be complex and dependent on a number of factors. Ideally, although not necessarily, the conformational structure formed is independent of crystallization conditions (Creighton, *Proteins*, 2nd Ed., W. H. Freeman, 1993). Analogy can be drawn to the folding of proteins, also highly sensitive to environmental conditions (Creighton, *Proteins*, supra).

Crystallization of proteins and other biomacromolecules, including biomacromolecules having secondary, tertiary, or quaternary structures, is typically difficult and time consuming (Creighton, *Proteins*, supra; McRee, *Practical Protein Crystallography*, supra). One reason is the low solubility of these compounds, which results in low solute concentration, which in turn lowers the probability of nucleation and crystal growth events. Other reasons include: high molecular weight and consequent slow diffusion; complex molecular shapes that must become precisely oriented; and generally weak intermolecular bonding. These factors lead to important conclusions regarding the differences between small molecules and macromolecules that pertain to the instant invention. First, larger molecules diffuse in solution more slowly than small molecules (see Atkins, *Physical Chemistry*, W. H. Freeman, 1998). This affects the kinetics of nucleation and crystal growth. The kinetics of crystal formation are affected by the diffusion coefficient to the extent that the process is diffusion controlled. Crystallization depletes the crystallizing moiety from solution near the liquid/crystal interface, so that fresh supplies of the moiety must diffuse from the bulk liquid for crystallization to continue. Consequently, small rapidly diffusing molecules are more likely to nucleate than are large molecules, and crystals of small molecules will generally grow faster than those of large molecules. The stochastic nature of nucleation suggests that multiple trials with identical nucleation-permissive conditions will yield some nucleation events; thus, for cases of difficult nucleation, a large number of duplicative experiments are justified. Many biomacromolecules are, however, difficult to make, isolate, and purify, so that the amounts available for combinatorial and duplicate crystallization experiments are commonly small.

Transmembrane proteins are particularly difficult to crystallize. These protein molecules span cellular membranes, so that the bulk of the molecule resides in the lipid-rich membrane itself, while parts of the protein extend into the aqueous cytoplasm and/or extracellular liquid. Such a protein, which has several hydrophobic and hydrophilic regions, generally has a complex conformation that depends on its native cellular environment. When removed from its native cellular environment into either an aqueous or non-aqueous liquid, its conformation changes drastically. Crystallization of transmembrane proteins in a manner that preserves their native structure is therefore a major challenge. Some such proteins, for example bacteriorhodopsin, have been crystallized using salt precipitation after solubilization and stabilization of the hydrophobic surfaces by octyl glucoside (Michel et al. (1980), *Proc. Natl. Acad. Sci. USA* 77:1283–5), a feat that earned the successful crystallographer the Nobel Prize. Alternatively, a technique termed two-dimensional electron crystallography (2DEC) images membrane proteins that form two-dimensional crystals or ordered arrays. Although 2DEC does not suffer from the phase problem of x-ray crystallography, the calculated structures are of low resolution. The current prevalence of 2DEC for obtaining transmembrane protein structural information reflects the difficulties in obtaining high-quality three-dimensional crystals.

One of skill in the art will immediately apprehend that, in addition to offering protein crystallization experiments using very low fluid volumes to increase rapidity and the number of experiments possible with limited amounts of protein, acoustic ejection of immiscible fluids may provide improved methods for creating two- and especially three-dimensional crystals of transmembrane proteins. For example, micelles containing anchored proteins may be deposited by acoustic ejection in sites having small fluid volumes (e.g., picoliters). Similar methods may be used to deposit phospholipid bilayer liposomes having different conditions inside and outside the liposome and having a transmembrane protein traversing the bilayer with portions inside and portions outside the liposome. Additionally, two-dimensional crystals of transmembrane proteins anchored or embedded in a bilayer can be ejected onto a substrate surface and stacked in arrangements permitting inter-protein interactions (for example, with an externally anchored protein) to attempt construction of appropriate three-dimensional crystals).

The detailed structures of proteins and other higher ordered structure biomacromolecules, including nucleic acids, may be more difficult to obtain by solution or other NMR techniques than by crystallographic methods. NMR methods are favored for smaller proteins or proteins that do not crystallize, such as Heat Shock Protein class proteins (HSPs), including steroid and retinoid receptors and Prion Protein (PrP) Three basic mechanisms are considered here by which a physical or chemical entity or condition, such as a chemical agent, can affect the crystallization process, and can thus increase the likelihood of forming crystals suitable for high-resolution x-ray crystallography. First, the physical or chemical entity or condition can promote crystal formation directly by affecting the thermodynamics or kinetics of crystallization. Second, the physical or chemical entity or condition can stabilize a particular conformation or prevent denaturation during crystallization. Third, a physical or chemical entity or condition can prevent amorphous aggregation of the polypeptide, thereby allowing folding into a structured conformation and crystallization.

Sometimes a physical or chemical entity or condition can serve multiple roles to increase the likelihood of obtaining crystallographic quality crystals. For example, dissolved ions (such as $Zn^{2+}$, $Na^+$) may be used to increase ionic strength to "salt out" the crystals by stabilization of the crystalline state. Urea, a chaotropic agent (i.e., one that disrupts structures, particularly hydrogen-bonded structures; chaotropic agents denature proteins but not DNA or RNA) may be used to prevent aggregation and also be a ligand. Other ligands that are not surfactants or chaotropic agents may still reduce aggregation by reducing unfolding events. A surfactant may be used to reduce aggregation of proteins having exposed hydrophobic surface and also to stabilize the native conformation of the protein. Indeed, non-ionic or zwitterionic surfactants, or ionic surfactants in the presence of a divalent ion having opposite charge to the surfactant ion, can promote crystallization as well as reduce aggregation and stabilize a native conformation in aqueous solutions.

The same chemical or physical condition can, under some circumstances, act in competing ways to both increase and decrease the likelihood of crystallization. For example, both high and low temperatures can reduce amorphous aggregation, but those skilled in the art of protein chemistry in general will immediately appreciate that both high and low temperatures can also increase denaturation, which can increase aggregation and destabilize native conformations.

Zinc finger DNA binding proteins have been crystallized and their structures determined to a high level of resolution in the presence of $Zn^{2+}$ and appropriate sequences of double stranded DNA. Such crystals comprise protein/DNA co-crystals, with the protein bound to the specific cognate DNA (Klug et al. (1995) FASEB J. 9(8):597–604). As described by Klug et al. (1995) supra, the requirement of $Zn^{2+}$ for DNA binding was first discovered fortuitously in an unusually abundant Xenopus transcription factor having a 30-residue repeated sequence motif, when a chelating agent (EDTA) removed $Zn^{2+}$ and other divalent cations and eliminated DNA binding capability. Ultimately, the hypothesis was substantiated that the repeated sequence motif, which came to be called the zinc finger motif, forms an independent minidomain containing a zinc ion, and that adjacent zinc fingers are combined as modules to make up a DNA-binding domain. The DNA sequence to which the Xenopus transcription factor binds were identified, permitting crystallization of the DNA-protein complex, leading to elucidation of the crystal structure.

Protein molecules may be fully or partially denatured even in the presence of a stabilizing ligand, by solvent conditions such as pH; chemical agents such as surfactants, guanidine and urea; and physical conditions such as temperature. In proteins having catalytic activity (i.e., enzymes), the enzymatic substrate acts as a structurally stabilizing ligand, though the substrate-bound conformation is not the only native conformation. Partially denatured proteins or polypeptides have at least one partially denatured domain, and include proteins having all domains fully denatured except for one partly denatured domain. A non-native structure in an enzyme may be identified by the enzyme's inactivity in the presence of its native substrate. Distinguishing native, disordered native, and denatured (non-native) structures in other proteins, including structural proteins, is generally more difficult.

All proteins other than those that are largely denatured, or large proteins that have no regular structure beyond their primary (sequence) structure, are generally considered crystallizable under suitable conditions. These conditions may include the presence of one or more ligands. The term "ligand" comprises inorganic and organic ions; small inorganic or organic molecules; and biopolymers, including oligo- and poly-peptides, oligo- and poly-nucleotides, peptidoglycans, and mucopolysaccharides. Examples of inorganic ion ligands include divalent cations such as $Mg^{2+}$, $Zn^{2+}$, and $Ca^{2+}$. Known examples of organic molecule ligands include steroids and retinoids, which can bind to a protein of the Heat Shock Protein (HSP) class.

Salts and other agents commonly used to induce biomacromolecule crystallization from solution, but in amounts considered insufficient to be termed precipitating agents, include calcium chloride dihydrate, tri-sodium citrate dihydrate, magnesium sulfate hexahydrate, ammonium acetate, ammonium sulfate, lithium sulfate monohydrate, magnesium acetate tetrahydrate, sodium acetate trihydrate, mono-potassium dihydrogen phosphate, zinc acetate dihydrate, calcium acetate hydrate, sodium chloride, hexadecyltrimethylammonium bromide, cobaltous chloride hexahydrate, cadmium chloride dihydrate, potassium sodium tartrate tetrahydrate, ferric chloride hexahydrate, mono-sodium dihydrogen phosphate, cesium chloride, zinc sulfate heptahydrate, cadmium sulfate hydrate, nickel(II) chloride hexahydrate, mono ammonium dihydrogen phosphate, and dioxane. The concentrations commonly used are readily ascertainable. These agents are commonly used at much higher concentrations as precipitants. As acoustic deposition permits dilution at the droplet, a wide variety of concentrations easily can be tried in combinatorial arrays.

Buffers commonly used for biomacromolecule crystallizations include, in appropriate concentrations that will be evident or readily obtained by one of ordinary skill, sodium acetate trihydrate (pH 4.6), tris hydrochloride (pH 8.5), HEPES (pH 7.5), TRIS (pH 8.5), HEPES—Na (pH 7.5), sodium cacodylate (pH 6.5), tri-sodium citrate dihydrate (pH 5.6), sodium acetate trihydrate (pH 4.6), and imidazole (pH 6.5). For the buffers, pH is that of a 1.0 M stock (0.5 M for MES) prior to dilution with other reagent components, and a typical concentration is 0.1 M. The pH may be adjusted with HCl or NaOH, as is common.

Precipitating agents commonly used for biomacromolecule crystallization include, in various concentrations and combinations that will be evident or readily obtained by one of ordinary skill, 2-methyl-2,4-pentanediol (MPD), potassium sodium tartrate tetrahydrate, mono-ammonium dihydrogen phosphate, ammonium sulfate, ammonium formate, sodium acetate, tri-sodium citrate dihydrate, 2-methyl-2,4-pentanediol, polyethylene glycol 400, polyethylene glycol 1000, polyethylene glycol 1500, polyethylene glycol 4000, polyethylene glycol 6000, polyethylene glycol 8000, polyethylene glycol 10,000, polyethylene glycol 20,000, polyethylene glycol monomethyl ether 2000, polyethylene glycol monomethyl ether 5000, polyethylene glycol monomethyl ether 550, ethylene imine polymer, tert-butanol, Jeffamine® C6007, sodium acetate trihydrate, isopropanol, ethanol, imidazole, 1,6-hexanediol, ethylene glycol, anhydrous glycerol, lithium sulfate monohydrate, sodium chloride, sodium formate, mono-sodium dihydrogen phosphate, magnesium formate, magnesium chloride hexahydrate, and dioxane.

Surfactants used for biomacromolecular crystallization include those that are anionic, cationic, zwitterionic, and non-ionic. Examples of commonly used surfactants include sodium dodecyl sulfate, sodium lauryl sulfate, glycerol, and octyl glucoside. Non-ionic surfactants such as glycerol and octyl glucoside are typically used to stabilize exposed hydrophobic surfaces and to solubilize proteins against precipitation. Chaotropic agents often used in protein chemistry include urea and guanidine.

Examples of combinations and concentrations of precipitants include: (i) 20% v/v isopropanol and 20% w/v polyethylene glycol 4000; (ii) 10% v/v isopropanol and 20% w/v polyethylene Glycol 4000; (iii) 2% v/v Polyethylene Glycol 400 and 2.0 M ammonium sulfate; (iv) 10% w/v polyethylene glycol 8000, 8% v/v ethylene glycol; (v) 10% w/v polyethylene glycol 6000, 5% v/v MPD; (vi) 2% w/v polyethylene glycol 8000; and (vii) 15% w/v polyethylene glycol 8000.

The ability of the invention to perform diluting and non-diluting additions of fluids to solutions of the biomacromolecule, crystallization reagents, known or putative ligands, and the like will be readily evident. For example, addition of water will dilute all moieties present in a droplet or reservoir in which experimental crystallization is being performed. Addition of water containing the biomacromolecule at the same concentration as in the experimental droplet will dilute all constituents of the droplet except the biomacromolecule. As mentioned above, because nucleation often requires higher protein or other biomacromolecule concentrations than are optimal for forming high-quality crystals, the in situ detection of nascent crystals offered by the instant invention may permit high-quality crystals to be produced in the first generation experiment, which is often a screening experiment.

Screening is often done in an array format using common precipitants in a wide range of concentrations and pH values (Stura et al. (1994) *Acta Crystallogr*. D50:448–55). A dilution method can often be used to reduce the number of array sites in a solubility-screening array. For example, McRee, *Practical Protein Crystallography*, supra, describes a dilution technique in which a solution containing precipitated protein is diluted with water, which may permit protein microcrystals that formed along with the amorphous precipitate to seed larger crystals as the precipitate dissolves. Acoustic ejection of minute volumes permits slow dilution and may permit the initial solubility-screening step to become a first generation crystallization experiment that yields high-quality crystals.

There are many scattering and absorption mechanisms for acoustic waves that propagate through a suspension of particles in a fluid medium. These include thermal transport losses, viscous drag, acoustic scattering and acoustic loss within the particles themselves. These absorption mechanisms are well described by Allegra et al. (1972) *Journal of the Acoustical Society of America* 51(5):1545–1564. For the acoustic frequency ranges of present interest, the dominant loss mechanism is expected to be acoustic scattering. Thus, as a coherent acoustic wave propagates through a particle suspension in a fluid, the wave is scattered from the particles, and that scattered energy is measured as a loss by a coherent receiving transducer. The particles may be, for example, protein crystals or salt crystals in a protein crystallization experiment. It will be shown below that acoustic scattering is expected to be much more sensitive to the presence of the protein crystals, and hence is a promising method of measuring protein crystal concentration, even in the presence of other background particles such as salt crystals.

The acoustic attenuation coefficient $\alpha_s$ in a fluid suspension, due to scattering, is described by the well-known relation:

$$\alpha_s = (\tfrac{1}{2}a)\epsilon k^4 a^4 (\tfrac{1}{3}[1-\kappa/\kappa']^2 + [(\rho'-\rho)/(2\rho'+\rho)]^2) \quad (1)$$

where $\epsilon$ is the volume fraction of particulate matter in the suspension, k is the acoustic wavenumber in the fluid ($k=2\pi/\lambda=2\pi f/c$, where $\lambda$ is the acoustic wavelength in the fluid, f is the acoustic frequency, and c the acoustic compressional velocity in the fluid), a is the radius of the particle, $\kappa$ and $\kappa'$ are, respectively, the bulk moduli of the fluid and particle, and $\rho$ and $\rho'$ are the mass density of the fluid and particle, respectively. Note that the acoustic attenuation coefficient varies as $k^4a^4$, which will be discussed in more detail later. Eq. (1) is valid for values of $(ka)<0.5$, and for reasonably dilute solutions, where multiple scattering events are negligible. For particles a few micrometers in size, this condition corresponds to an acoustic wavelength of $\lambda \sim 10$ um in the fluid. With a typical fluid velocity of 1500 m/s, this in turn corresponds to an acoustic frequency of 150 MHz. Thus, the above relation may be expected to be valid for acoustic frequencies <150 MHz and for particles several micrometers in size.

We now show that acoustic scattering is expected to be much stronger for protein crystals than for salt-type crystals. The bulk modulus and density for a protein crystal are taken to be $4.5e07$ N/m$^2$, and $0.6e03$ Kg/m$^3$, respectively. The bulk modulus and density for a salt crystal are taken to be 1.e11 N/m$^2$, and 2.2e03 Kg/m$^3$, respectively. The bulk modulus and density for a water-like fluid are taken to be 2.3e09 N/m$^2$, and 1e03 Kg/m$^3$, respectively. Inserting these values into Eq. (1), we obtain the following acoustic attenuation coefficients in the fluid:

Protein in water: $\alpha_s = 420 \, \epsilon k^4 \, a^3 \, [m^{-1}]$

Salt in water: $\alpha_s = 0.2 \, \epsilon k^4 \, a^3 \, [m^{-1}]$

It is clear therefore that the attenuation coefficient is about 2000 times larger for the suspension of protein crystals than for the suspension of salt crystals. Thus, for comparable volume concentrations, the acoustic attenuation will be dominated by scattering from the protein crystals. Note that this large difference in the scattering behavior between the protein and salt crystals is due primarily to the difference in the bulk moduli of the two materials.

It is noted in passing that the acoustic velocity in the protein crystals is 275 m/s, while the acoustic velocity in the salt is 6700 m/s. For dilute solutions, the acoustic velocity of the suspension will be altered from that of the pure fluid by an amount proportional to the volume concentration of the particles multiplied by the acoustic velocity of the particles. Thus, it would be expected that the presence of suspended protein crystals would reduce the overall acoustic velocity of a fluid, while the velocity of a fluid would be increased by the presence of suspended salt crystals. Hence acoustic velocity information, which would inherently be available from an attenuation measurement, would also provide information concerning the presence of suspended protein and salt crystals.

Eq. (1) is valid for values of (ka)<0.5. For larger values of ka, the attenuation coefficient becomes less strongly dependent on the value of (ka), and for (ka)>>1, the attenuation coefficient is independent of acoustic frequency. Thus, there is a notable change in the dependence of the attenuation coefficient a, on (ka), which occurs at (ka)~1. It may be possible to use this change to determine the size of the protein crystals in a suspension, for example by sweeping the acoustic frequency over a range of values corresponding to values of (ka) below and near unity. The attenuation measured over this frequency range would then have a characteristic dependence (for example, proportional to f$^4$ at lower frequencies, and becoming less dependent on f as (ka) approached unity). Such an acoustic frequency sweep could be made within one tone burst pulse, commonly termed a chirped tone burst, and the received acoustic signal could then yield information concerning both the presence and size of the protein crystals in a fluid suspension. It is useful that the condition ka~1 occurs in water for acoustic frequencies of order ~100 MHz, for particles of micrometer dimensions.

Acoustic detection is an especially important aspect of the instant invention, because an acoustic transducer is already employed for manipulating the solutions of biomacromolecules and reagents for crystallization. Thus, acoustic in situ detection of suspended particles in a combinatorial array of the invention is feasible with the mere addition of acoustic sensors or other data gathering means. Acoustic sensors need not be bulky. Furthermore data sampling can be performed almost instantaneously after ejection, facilitating, for example, dilution experiments. In such experiments, the dissolution of precipitate and the growth of crystals can be ascertained immediately after each dilution step and then periodically thereafter, and the decision whether to dilute further may be made quickly, avoiding possible overdilution (which may arise with the use of traditional optical methods that may be unable to detect the initial formation of microcrystals). Otherwise, decisions on such dilutions would probably occur after considerable time to determine whether crystals were growing.

The advances in x-ray sources that permit crystal structure determination on increasingly small crystals also permit in situ diffraction experiments on crystals in a dense array format. Instead of recording sufficient data to solve the structure, such experiments can be designed to scan the sites where biomacromolecule crystals have formed, as determined by acoustic methods, and determine whether the diffraction quality would yield high-resolution crystallographic structures if enough diffraction data were taken. Whether a crystal has reached the minimum size for high-resolution diffractometry can be determined acoustically. An integrated system employing acoustic fluid droplet manipulation, in situ acoustic detection of biomacromolecule crystals, and in situ assessment of crystal quality is feasible. In some cases after determination of crystal quality, dilution methods may be employed to attempt in situ re-crystallization to form higher quality or larger crystals. Methods that control vapor diffusion may be employed to slow crystal growth, including the microbatch methods that cover the experimental droplet with oil and the vapor diffusion control method of capping the reservoir with oil. These methods have been described above and some are described in more detail in the examples that follow.

One of ordinary skill will appreciate that other aspects of protein crystal production are encompassed by the invention although not described in detail. For example, protein crystals having metal substituents may be generated by trial and error, with acoustic deposition permitting combinatorial experimentation with metal solutions and crystalline fragments. A convenient way to test for metal substitution would be to employ arrays of metal solutions as described herein. Determining ligands may also be accomplished by array methods facilitated by acoustic deposition; the arrays may comprise solutions of metals as well as biomolecules. (Insulin was first only crystallizable when stored in a galvanized bucket, and the requirement for divalent zinc as a structuring ligand was later established.) The mounting of crystals in capillary tubes and the manipulation of crystals stored under liquid nitrogen are also facilitated, as is experimentation with cryoprotectants used for cold storage protection of proteins. Determining the conditions favoring amorphous aggregation is also facilitated by combinatorial acoustic deposition methods. Because of the reduced time scale for experiments involving picoliter-size volumes, a wide variety of temperatures may be employed for crystallization experiments, with a resultant low concern for thermal or microbial degradation. Sodium azide (NaN$_3$) is often employed to inhibit microbe growth and has been shown to reduce crystal quality, and a decrease in time required to complete experiments (to less than the typical generation time of microbes) may allow its use to be decreased. Finally, the likelihood exists that acoustic energy may be employed to crush small crystals for seed.

It is to be understood that while the invention has been described in conjunction with the preferred specific embodiments thereof, the foregoing description is intended to illustrate and not limit the scope of the invention. Other aspects, advantages, and modifications will be apparent to those skilled in the art to which the invention pertains.

All patents, patent applications, journal articles, and other references cited herein are incorporated by reference in their entireties.

The following examples are put forth so as to provide those of ordinary skill in the art with a complete disclosure and description of how to implement the invention, and are not intended to limit the scope of what the inventors regard as their invention. Efforts have been made to ensure accuracy with respect to numbers (e.g., amounts, temperatures, etc.), but some errors and deviations should be accounted for. Unless indicated otherwise, parts are parts by weight, temperature is in degrees Celsius, and pressure is at or near atmospheric.

EXAMPLE 1

Microbatch Crystallization:

An experiment is conducted using a matrix of 15360 separate crystallization conditions to attempt to crystallize a small amount of a protein isolated and purified from rat brain tissue. The protein's sequence is known, but attempts to express the protein in E. coli have failed due to aggregation of unfolded protein. Heuristic sequence homology analysis and computational modeling indicate that the protein may be in the HSP class. Spectroscopic techniques reveal a significant amount of secondary structure. Native PAGE and SDS PAGE confirm the isolate to be a single polypeptide of high purity and having a significant degree of native conformational structure under non-denaturing conditions. Ligand screening by conventional methods does not reveal any ligands.

The protein concentration is in the range of 1.5 to 200 mg/mL. The total small fluid volume is 40 picoliters (pL) for each separate crystallization trial and requires approximately $7.5 \times 10^{-3}$ µg of protein for the entire trial (for average small volume protein concentration of about 14 mg/mL). For convenience, the drops are ejected upward onto the underside of a silanized glass plate. Several solutions are combined into the final 40 pL drop to create 15360 unique experiments. It will be readily apprehended that these experiments may be performed in duplicate, triplicate, or other redundant modes as desired. Different buffering reagents employed include sodium acetate, sodium citrate, 2[N-morpholino]ethanesulfonic acid (MES), N-[2-hydroxyethyl]piperazine-N'-[2-ethanesulfonic acid] (HEPES), TRIS (tri[hydroxymethyl]amino-methane, and sodium borate. Polymers include polyethylene glycol (PEG) 6000, PEG 8000, PEG 10,000, PEG 20,000, PEG monomethyl ether (PEG MME) 550, PEG MME 2000, PEG MME 5000, Jeffamine M-600, and Jeffamine ED-2001. Salts and metal salts employed include ferric chloride, ammonium sulfate, cesium chloride, zinc sulfate heptahydrate, and nickel (II) chloride. Organic additives tested for their ability to increase the likelihood of forming crystallographic-quality crystals include dioxane, imidazole, 1,6 hexane diol, tert-butanol, anhydrous glycerol, ethanol, and ethylene glycol. Instead of employing a pure combinatorial approach (see preceding examples), a heuristic combinatorial approach is employed using known crystallization conditions for sequence-homology-related proteins, obtained from the Biological Molecule Crystallization Database (NIST/CARB BMCD). The data obtained from this database permit narrowing the combinatorial experiments to 15,360 by an appropriate choice of reagents. The BMCD data indicate that a macromolecular structuring ligand is unlikely: the structurally closest homologous proteins do not require a ligand to form high-quality crystals, and the known structures of these proteins have no biomolecular ligands.

The reagent formulations or crystallization mixtures are dispensed in a combinatorial fashion, as described in the preceding examples, to create as many as 3840 different buffer compositions. These buffer compositions are contained in separate containers, namely well plate wells. Three 1536 well plates provide adequate storage for 3840 separate solutions. Solution volumes of 5 µL total per well will provide more volume than is required for all the different crystallization trial experiments. In addition, crystallization trials will take place at both 25° C. and 4° C. and at protein concentrations of 50 mg/mL and 5 mg/mL. Therefore, a total of ten, 1536 well plates will be used to contain 15360 separate crystallization trials. 20 pL of protein solution will be combined with 20 pL of already made buffer solution to create the final drop formulations or trial drops.

To prevent rapid vapor diffusion of the trial 40 pL drops, a microbatch technique is adapted to the picoliter volume scale attainable by focused acoustic ejection, rendering a "picobatch" technique. The technique employs oils to vary the rate of vapor diffusion. In a standard vapor diffusion setup using a hanging or sitting drop, paraffin oil overlies the experimental drop (Chayen et al. (1990) J. Appl. Cryst. 23:297). The modified microbatch technique employs a mixture of paraffin and silicone oils (D'Arcy et al. (1996) Journal of Crystal Growth 168:175–80). In the vapor diffusion rate control method (Chayen et al. (1997) J. Appl. Cryst. 30:198–202), 200 microliters of oil is applied over the reservoir solution for standard-sized droplet reservoir wells. In each of these methods, the oil acts as a barrier to vapor diffusion between the reservoir and the drop. Paraffin oil permits such limited kinetics of vapor diffusion that the drop behaves as a batch experiment. Silicone oil renders results more similar to those when no oil is used. The conventional microbatch methods require that the experimental droplet be pipetted under the layer of oil. Using a mixture of paraffin oil and silicone oil permits fine adjustment of the rate of vapor diffusion between the drop and the reservoir. The rate of vapor diffusion is also a function of the thickness of the oil layer placed over the droplet or reservoir or both.

In the microbatch techniques, a drop is encapsulated in a mixture of paraffin oil and silicone oil. The higher the fraction of paraffin oil, the slower the vapor diffusion rate. A 2:1 ratio of paraffin oil to silicone oil is used in these particular experiments.

To prevent evaporation of the solutions, the oil mixture is dispensed over the crystallization mixtures prior to ejection to the silanized substrate above the wells containing the crystallization mixtures. Ejecting both the crystallization and the protein solutions through an overlying layer of immiscible oil, the trial drops will be rapidly encapsulated in the oil mixture. This rapid encapsulation will slow the rate of vapor diffusion and enable crystal formation.

To complete the setup of the crystallization trials, five 1536 plates containing 7680 trial drops will be placed at 4° C. and the other 7680 trial drops will be placed at 25° C. The drops may be scanned acoustically for the formation of amorphous precipitate, protein crystals, or buffer crystals. Drops that evidence protein crystal formation may be readily distinguished from buffer salts by their different acoustic scattering properties. Acoustic microscopy may also be used to distinguish amorphous precipitate from crystals based on particle size. Typically, crystal diameters far exceed the size of amorphous precipitate particles consisting of denatured or aggregated protein. Once crystals have been located, they may be removed from the trial drops and used for preliminary diffraction experiments to determine the quality of diffraction. Alternatively, microcrystals may be acoustically ejected to a series of drops containing new combinations of crystallization reagents and the protein, to be used as seed crystals for further crystallization trials.

EXAMPLE 2

Combinatorial Optimization of Crystallization Conditions for a Protein with Conformational Flexibility (I):

In many crystallization experiments, an attempt is made to find solvent conditions that produce homogeneous crystals that yield a diffraction pattern that permits solving the crystal structure to a high degree of resolution (e.g., a resolution of 3.5 Å or less). An inherent conformational flexibility of the protein may inhibit or prevent the formation of crystals. For example, prion protein in the cellular conformation (PrPC) is difficult to crystallize. $PrP^C$ has a predominantly random coil structure, with the quaternary structure being a rather random configuration of the random coil domain and a single-folded domain having conventional secondary and tertiary structure (Liu et al. (1999) supra; Zahn et al. (2000) *Proc Natl Acad Sci USA* 97(1):145–50). Using unfolding experiments, Jackson et al. (1999) *Biochim BiophysActa* 1431(l):1–13, showed that the structure of heterologously expressed PrP depends upon solvent conditions, with the disulfide bond-reduced sequence capable of assuming both $PrP^C$-like and a scrapie conformer ($PrP^{Sc}$)-like structure depending on pH. Thus, the possibility exists that the random coil structure could be converted into a non-random and consequently crystallizable structure, either by the selection of suitable solvent conditions or through the use of an as yet undiscovered ligand, or by a combination of both. The search for appropriate solvents, ligands, and other microenvironmental conditions may be complemented by the use of variants of the protein that might form high-quality crystals. An example of this approach is provided by early studies of myoglobin (Kendrew, J. C. and Parrish, R. G. (1956) *Proc. R. Soc. Lond. A* 238:522–527). These studies found that sperm whale myoglobin produced high-quality crystals, while other myoglobin variants failed to crystallize. Since sperm whale myoglobin has a high degree of sequence homology to human myoglobin, structural inferences could be made to the human form.

Similarly, single amino acid substitution variants of PrP have been demonstrated to have different structural stability characteristics (see, e.g., Calzolai et al. (2000) *Proc Natl Acad Sci USA* 97(15):8340–45).

In conjunction with the methods of the instant invention, a mutant library of proteins may be created via standard techniques (site-directed mutagenesis, error-prone PCR, directed evolution, and the like), and small quantities of protein may be expressed and isolated. The resulting library of proteins may then be conveniently isolated by including a glutathione-S-transferase, or other convenient affinity tag. A large matrix of 5000 proteins could be subjected to 1000 different conditions, requiring 5,000,000 different hanging drop experiments without duplication.

Using picoliter drop technology and a non-diluting approach, this would require the creation of 50 drop well plates, each containing 100,000 different solutions. With a protein and crystallization solution diluting approach, 5000 protein solutions and 1000 crystallization condition solutions could be employed, using standard 1536 well plates to form arrays on coverslips placed over conventional hanging drop setups. For the hanging drop array method, 40 pL droplets would be arrayed at a density of about 10,000/$cm^2$, as is evident from the preceding examples. Such a setup would use about a 7 mm×7 mm square area of an 18 mm diameter coverslip, permitting 5000 experimental sites per hanging drop container, thus requiring a total of 1000 conventional hanging drop containers. Either approach is practicably attainable. Oil coating of droplets is possible for both methods. The reservoirs of the hanging drop setups can also be capped with oil (vapor diffusion method). The drop well plates can be placed in contact with a fluid reservoir, which can be capped with oil. Alternatively, 100 drop well plates can be employed, with every other well containing only solvent.

Both techniques are employed with 10-fold duplication of each experiment. Because $PrP^{Sc}$ has considerable hydrophobic β sheet content, the $PrP_C$-containing solutions are not contacted with any oil. The hanging drop reservoirs are, however, capped with oil. To vary conditions, the drop well method using every other well as a solvent reservoir is employed and no oil is added to control diffusion. The initial experiments are conducted by mutating hPrP(121–230). Instead of random combinatorial mutation of the entire sequence, error prone PCR is performed on the cDNA sequences coding the amino acid sequence regions of PrP (121–230) already shown to be less structured and susceptible to being more structured, plus flanking regions. The mutated sequence segments are then ligated to the rest of the coding cDNA sequence to produce the experimental proteins.

The drop well plates or hanging drop coverslip arrays may be rapidly scanned for nascent crystals via scanning acoustic microscopy. Buffer crystals and protein crystals are conveniently separated by this method. Wells or hanging droplets in which any nascent crystals are detected are diluted slightly. The drop wells or array sites containing protein crystals are further evaluated for crystal quality by scanning diffractometry. High quality crystals are collected, and more of the proteins that result in the formation of high-quality crystals are synthesized, and the resulting crystals used as seeds in scaled-up crystallization experiments, as necessary. Those protein crystals that are not of diffraction grade are diluted slightly for recrystallization. Array sites containing amorphous precipitate or amorphous precipitate plus microcrystals are also diluted, and they are evaluated acoustically and by scanning diffractometry.

EXAMPLE 3

Combinatorial Optimization of Crystallization Conditions for a Protein with Conformational Flexibility (II):

A conformationally labile protein such as PrP may be co-crystallized in the presence of an antibody or ligand that provides structural stability required to promote the growth of high-quality crystals. Additionally, studies of the protein complexed with a biologically relevant ligand may provide useful information about biological behavior and function. An example of the productive use of this technique towards obtaining high quality crystals is the complex between lambda repressor and DNA (Jordan et al. (1985) *Science* 230:1383–1385). To obtain crystals, the composition of the lambda repressor ligand, a DNA binding sequence, was systematically varied.

Randomized DNA may be produced synthetically by conventional phosphoramidite DNA chemistry. In cases where a large matrix of conditions is required to obtain homogeneous crystals, 50,000 ligand variants could be combined with a protein and subject to 1000 solvent conditions for crystallization trials. This would mean a total of 50,000,000 different conditions and require 500 drop well plates, each containing 100,000 different samples. If necessary, the density of the drop well plate may be changed, and a 25 mm×75 mm plate can readily accommodate over 1,000,000 drops. This method reduces the number of required plates to 50 for the experiment described herein.

Alternatively, the method described in the preceding example may be employed, requiring 10,000 conventional hanging droplet containers. Because the solvent may be added to each container by machine, this technique is practicable, but the solvent-reservoir-free approach is more convenient for a first generation experiment. Proteins that did not yield crystals suitable for high-resolution x-ray diffraction, even after post-crystallization dilution, may be crystallized by the hanging array method, with and without seeding. The experimental wells and/or array sites may be evaluated acoustically for crystal quality by the methods described in the preceding example or elsewhere hereinabove, and further manipulations such as dilution may be performed.

EXAMPLE 4

Method for Modified Microbatch Crystallization:

As described in Example 5 herein, oil on droplets, in reservoir wells, or both may be used to control rates of vapor diffusion. Control of rate of vapor diffusion by coating with paraffin oil the experimental drops used in hanging or standing drop methods was demonstrated by Chayen et al. (1990) supra. As solvent diffusion into or out of the droplet is very slow, the droplet remains substantially static, explaining the use of the term "microbatch". D'Arcy et al. (1996) supra, uses silicone fluids that are polymers of —$(Si(CH_3)_2$—$O$—$)_n$—, for a modified oil coating method that allows more diffusion. One can thus perform an experiment under oil and have diffusion from an aqueous solvent through the oil. Chayen et al. (1997) supra, introduced a method whereby the reservoir fluid is coated with an overlying oil layer, which can be adjusted for both composition and thickness, and combined with the microbatch methods that control diffusion by coating the droplet. In the preceding example, the protein solutions were diluted with the combinatorial crystallization buffer solutions. The instant example teaches an ejection technique wherein the protein is not diluted, and the entire crystallization experimental solution is pre-mixed in well plate wells.

Paraffin oil is ejected or otherwise aliquotted into a 1536 well plate that contains a protein dissolved in a variety of different solvent conditions. Among the parameters that are varied in the solution are pH, protein concentration, concentration of PEG, and ionic strength. The protein solution is ejected through the immiscible paraffin oil layer onto a receiving substrate surface. This procedure results in a protein solution encapsulated in an immiscible oil. Additionally, a second oil such as a silicone oil may be ejected onto the existing protein drops. The addition of a second oil layer to the paraffin oil layer provides a means of controlling the rate of vapor diffusion from the protein solution. The more silicone oil in the paraffin/silicone oil mixture, the greater the rate of vapor diffusion. The use of a flat receiving plate allows for the simultaneous screening of a greater variety of crystallization conditions than the 1536 conditions that may be screened in the well plate. For drop volumes of 50 picoliters, over 1,000,000 drops may be screened in the area of a conventional 1536 well plate.

The protein chosen for this method is the PrP(121–230) mutation yielding the highest quality, albeit still too small, crystal from preceding Example 6. Because of concerns regarding contacting oil to the protein solution, a parallel experiment is performed using a standing droplet setup in which no oil contacts the protein solution. This experiment employs a density of about 10,000/cm² on a 7 mm×7 mm area of each coverslip, and 200 conventional standing drop setups, analogous to the hanging array described in preceding examples. The solvent for this standing array method is capped with the same oil mixture employed for the modified microbatch method (vapor diffusion control method). The paraffin and silicone oils can be combined in different ratios to control vapor diffusion rates, as previously mentioned.

EXAMPLE 5

Single-reservoir-per-hanging-drop Array Crystallization of a DNA Binding Transcription Factor Complexed to Cognate DNA:

A newly isolated frog transcription factor is isolated and expressed in a prokaryote by conventional methods. Sequence homology indicates the protein is a member of the zinc finger DNA binding protein family. Non-denaturing PAGE in the presence of excess zinc establishes several different conformers with different mobilities. Addition of EDTA to the non-denaturing PAGE reduces the observed electrophoretic pattern to a single mobility band, as is observed by standard PAGE, thus establishing that several conformations of the pure protein exist rather than impurities. NIST/CARB BMCD is accessed to provide information as to crystallization conditions and bound DNA sequences for homologous proteins. With knowledge as to the binding sequences of homologues, a heuristic combinatorial (e.g., not varying strong consensus nucleotides) ssDNA array is constructed by acoustic deposition, as described in a preceding example, with the DNA sequence covalently attached to the substrate surface. Routine methods of synthesizing DNA are used to synthesize all complementary sequences and an array of dsDNA is formed by stringent hybridization with reannealing to increase the stringency of complementarity.

The array is contacted with a thin overlying aqueous layer of the protein solution, under physiologic conditions and in the presence of $Zn^{2+}$. An infrared video camera is used to image the array and, after integration of the signal over time, those sites releasing the most heat are identified. The DNA sequences of the hottest sites are tested for binding, identifying the best-binding DNA as ascertained by differential scanning calorimetry (DSC). The binding constant as determined by DSC is used to determine the correct excess of DNA to bind substantially all the protein, without there being such a great excess that crystallization is inhibited. Non-denaturing PAGE in the presence of this amount of DNA reveals a single mobility band and no discernable signal from conformers not binding DNA.

The hanging array described in previous examples is employed to attempt to crystallize the protein. The information from NIST/CARB BMCD on similar crystallized complexes permits employment of a heuristic combinatorial crystallization strategy, employing 10,000 crystallization conditions. Each experiment is duplicated 10 times for a total of 100,000 experiments. Twenty conventional hanging drop containers each containing an array of 5,000 hanging picoliter-size droplets, at a density of about 10,000 droplets per square centimeter, are employed. Of the experiments demonstrated to yield protein/DNA co-crystals, several are shown to yield high-quality crystals that are too small for x-ray structural analysis. The conditions are scaled up and the small crystals are acoustically ejected directly from their array sites into the scaled-up droplets. The second-generation scaled-up experiment yields several high-quality crystals large enough for x-ray crystallographic analysis. Knowledge of the crystallization conditions also permits crystallization of specifically substituted heavy metal carrying amino acids for phasing as an aid to structural analysis.

EXAMPLE 6

Transmembrane Protein Crystallization:

A transmembrane protein isolated from Xenopus neural tissue is expressed in a prokaryote. The protein is only soluble in aqueous solution with a surfactant. Sequence homology analysis reveals that the protein is in the rhodopsin family. The protein forms 2-D arrays easily; the protein in a phospholipid bilayer gives low-resolution structure data using electron diffraction crystallography. Non-denaturing PAGE (in the presence of adequate non-ionic surfactant) establishes that the protein is pure and structured. NIST/

CARB BMCD data on the most homologous protein crystallized in 3-D permits a heuristic combinatorial approach using salts and non-ionic surfactants, including octyl glucoside, which employs the hanging array of previous examples. The solvent reservoirs for the hanging array method are capped with oil of varying compositions. The highest quality crystals are obtained using a 50/50 paraffin/silicone oil ratio, but are too small to use for x-ray structure analysis.

These crystals are used to scale up the experiments to yield high quality crystals sufficiently large high-resolution x-ray crystallographic analysis. Some of the small crystals are combinatorially interacted with heavy-metal solutions. These interactions produce instances of heavy-metal isomorphous replacement (McRee, *Practical Protein Crystallography*, supra). Isomorphously replaced crystals of appropriate size are obtained permitting solution of the structure to a resolution of 2.5 Å.

We claim:

1. A method for generating at least one fluid sample having a volume of no more than about 100 microliters on a substrate, containing a moiety of interest for crystallization and having a known composition, comprising
    positioning an acoustic ejector in acoustic coupling relationship with a reservoir of fluid, and
    directing acoustic radiation from the ejector into the reservoir, thereby acoustically depositing one or more reagent-containing fluid droplets at a site on the substrate surface,
    wherein at least one of the ejector and the reservoir is movable relative to the other, at least one of the reagent-containing fluid droplets deposited at the site contains the moiety of interest for crystallization, and at least one of the reagent-containing fluid droplets contains an agent that increases the likelihood of crystal formation.

2. The method of claim 1 further comprising a step for detecting whether the moiety of interest for crystallization has formed crystals.

3. The method of claim 1 or 2 further comprising controlling the temperature of the substrate and the ambient temperature and pressure surrounding the reagent-containing droplets and the fluid samples.

4. The method of claim 2 wherein the detecting step is carried out acoustically.

5. The method of claim 4, wherein each fluid sample contains polyethylene glycol and dimethyl sulfoxide.

6. The method of claim 1 wherein an array of fluid samples, each having a known composition and known chemical and physical conditions and containing the moiety of interest for crystallization, is generated on the substrate surface.

7. The method of claim 6 wherein each sample has a different known composition and different known chemical and physical condition.

8. The method of clam 6 wherein at least one of the fluid samples contains one or more crystallization promoting agents selected from the group consisting of inorganic salts, organic salts, organic non-polymeric molecules, and polymers.

9. The method of claim 1 wherein at least one of the reagent-containing fluid droplets deposited at the site contains one or more crystallization-promoting agents selected from the group consisting of inorganic salts, inorganic molecules, organic salts, organic non-polymeric molecules, and polymers.

10. The method of claim 9 wherein the crystallization-promoting agent is a surfactant or chaotropic agent.

11. The method of claim 10 wherein t e moiety of interest for crystallization is stabilized by the a surfactant or chaotropic agent.

12. The method of claim 11 wherein the moiety of interest comprises a biomacromolecule.

13. The method of claim 1 wherein the moiety of interest for crystallization is stabilized in a specific conformation by a ligand.

14. The method of claim 1 wherein the moiety of interest for crystallization comprises a biomacromolecule.

15. The method of claim 14 wherein the biomacromolecule comprises a partially or fully native protein domain.

16. The method of claim 15 wherein the biomacromolecule additionally comprises a fully denatured protein domain.

17. The method of claim 14 wherein the biomacromolecule is stabilized in a specific conformation by a ligand selected from the group consisting of ions, non-polymeric molecules, and biopolymers.

18. The method of claim 17 wherein the ligand comprises a divalent cation, a steroid, a retinoid, or a biopolymer comprising a sequence of monomers, the monomers selected from the group consisting of monosaccharides, amino acids, and nucleotides.

19. The method of claim 17 wherein the ligand is an ionic constituent of a salt that functions as a crystallization-promoting agent.

20. The method of claim 11, 13 or 17 further comprising a step for detecting whether the moiety of interest for crystallization has formed crystals.

21. The method of claim 14 wherein at least one of the reagent-containing fluid droplets deposited at the site contains a second biomacromolecule.

22. The method of claim 1 wherein the fluid samples and the reagent-containing droplets have a volume of up to about 1 micro liter.

23. The method of claim 22, wherein the fluid samples have a volume of about 1 picoliter to 30 nano liters and the reagent-containing droplets have a volume of about 0 1 picolitey to 10 nanoliters.

24. A method for generating at least one fluid sample having a volume of no more than about 100 microliters on a substrate, the fluid sample containing a moiety of interest for crystallization and having a known composition, and determining whether the known composition in combination with known chemical and physical conditions favor crystallization of the moiety of interest, the method comprising the steps of:
    (a) positioning an acoustic ejector in acoustic coupling relationship with a reservoir of fluid, and directing acoustic radiation from the ejector into the reservoir, thereby depositing one or more reagent-containing fluid droplets at a site on the a substrate surface, wherein at least one of the ejector and the reservoir is movable relative to the other, and at least one of the reagent-containing fluid droplets deposited at the site contains the moiety of interest for crystallization; and
    (b) detecting the presence and quantity of crystalline material composed of the moiety of interest in the fluid sample at the site.

25. The method of claim 24 further comprising:
    (c) depositing by focused energy ejection one or more reagent-containing fluid droplets at a site on a substrate surface having at least one fluid sample previously deposited at the site, and
    (d) detecting for the presence and amount of crystals of the moiety of interest in the at least one fluid sample at the site.

26. The method of claim 25 wherein said detecting step further comprises periodic detection of the amount size of crystals.

27. The method of claim 24, 25, or 26 wherein said detecting step is carried out acoustically.

28. The method of claim 27 wherein each fluid sample contains polyethylene glysol and dimethyl sulfoxide.

29. The method of claim 24, or 25 27 wherein an array of fluid samples, each having a known composition and a known chemical and physical conditions and containing the moiety of interest for crystallization, is generated on the substrate surface.

30. The method of claim 29 wherein at least one of the reagent-containing fluid droplets deposited at the site contains one or more crystallization promoting agents selected from the group consisting of inorganic salts, inorganic molecules, organic salts, organic non-polymeric molecules, and polymers.

31. The method of claim 30 wherein the moiety of interest for crystallization is a biomacromolecule, wherein the biomacromolecule is stabilized in a specific conformation by a ligand selected from the group consisting of ions, non-polymeric molecules and biopolymers.

32. The method of claim 31 further comprising independently controlling the temperature of the substrate and the ambient gas temperature and pressure surrounding the reagent-containing droplets and the fluid volumes samples.

33. The method of claim 24 wherein at least one of the reagent-containing fluid droplets deposited at the site contains one or more crystallization promoting agents selected from the group consisting of inorganic salts, organic salts, organic non-polymeric molecules, and polymers.

34. The method of claim 33 wherein the crystallization-promoting agent is a surfactant or chaotropic agent.

35. The method of claim 34 wherein the moiety of interest for crystallization is stabilized by the surfactant or chaotropic agent.

36. The method of claim 24 wherein the moiety of interest for crystallization is a biomacromolecule, the biomacromolecule being stabilized in a specific conformation by a ligand selected from the group consisting of ions, non-polymeric molecules, and biopolymers.

37. The method of claim 36 wherein the ligand comprises a divalent cation, a steroid, a retinoid, or a biopolymer comprising a sequence of monomers, the monomers selected from the group consisting of monosaccharides, amino acids, and nucleotides.

38. The method of claim 36 wherein the ligand is an ionic constituent of a salt that functions as a crystallization-promoting agent.

39. The method of claim 36 wherein the biomacromolecule comprises a partially or fully native protein domain.

40. The method of claim 39 wherein the biomacromolecule comprises a native protein.

41. The method of claim 39 wherein the biomacromolecule additionally comprises a fully denatured protein domain.

42. The method of claim 36 wherein at least one of the reagent-containing fluid droplets deposited at the site additionally contains a polypeptide.

43. The method of claim 42 further comprising a step for detecting whether the polypeptide has formed crystals.

44. The method of claim 43 wherein said detecting step is carried out acoustically.

45. The method of claim 24 further comprising independently controlling the temperature of the substrate and the ambient temperature and pressure surrounding the reagent-containing droplets and the fluid samples.

46. The method of claim 24 or 29 wherein the fluid samples and the reagent-containing droplets have a volume of, of up to about 1 microliter.

47. The method of claim 46 wherein the fluid samples have a volume of about 1 picoliter to 30 nanoliters and the reagent-containing droplets have a volume of about 0.1 picoliter to 10 nanoliters.

48. A method for generating at least one fluid sample having a volume of no more than about 100 microliters on a substrate, containing a biomacromolecule of interest for crystallization and having a known composition and known chemical and physical conditions, comprising positioning an acoustic ejector in acoustic coupling relationship with a reservoir of fluid, and directing acoustic radiation from the ejector into the reservoir, thereby acoustically depositing one or more reagent-containing fluid droplets at a site on the substrate surface, wherein at least one of the ejector and the reservoir is movable relative to the other, and at least one of the reagent-containing fluid droplets deposited at the site contains the biomacromolecule of interest for cystallization.

49. The method of claim 48 further comprising a step for detecting whether the biomacromolecule of interest for crystallization has formed crystals.

50. The method of claim 49 wherein the detecting step is carried out acoustically.

51. The method of claim 50 wherein each fluid volume sample contain polyethylene glycol and dimethyl sulfoxide.

52. The method of claim 48 wherein an array of fluid samples, each having a known composition and known chemical and physical conditions and containing the biomacromolecule of interest for crystallization, is generated on the substrate surface.

53. The method of claim 48 or 52 wherein at least one of the reagent-containing fluid droplets deposited at the site contains one or more crystallization promoting agents selected from the group consisting of inorganic salts, organic salts, organic non-polymeric molecules and polymers.

54. The method of claim 53 wherein the crystallization-promoting agent is a surfactant or chaotropic agent.

55. The method of claim 53 wherein the biomacromolecule of interest for crystallization is stabilized by the surfactant or chaotropic agent.

56. The method of claim 53 wherein the biomacromolecule of interest for crystallization is stabilized in a specific conformation by a ligand selected from the group consisting of ions, non-polymeric molecules, and biopolymers.

57. The method of claim 56 wherein the ligand comprises a divalent cation, a steroid, a retinoid, or a biopolymer comprising a sequence of monomers, the monomers selected from the group consisting of monosaccharides, amino acids, and nucleotides.

58. The method of claim 56 wherein the ligand is an ionic constituent of a salt that functions as a crystallization-promoting agent.

59. The method of claim 56 wherein at lease one of the reagent-containing fluid droplets deposited at the site contains a second biomacromolecule.

60. The method of claim 48 wherein the biomacromolecule of interest comprises a native protein domain or a partially denatured protein domain.

61. The method of claim 60 wherein the biomacromolecule of interest comprises a native protein.

62. The method of claim 64 wherein the biomacromolecule of interest comprises a partially native protein domain.

63. The method of claim 61 wherein the biomacromolecule of interest additionally comprises a fully native protein domain.

64. The method of claim 60 wherein the biomacromolecule of interest additionally comprises a fully denatured protein domain.

65. The method of claim 48 wherein the biomacromolecule of interest for crystallization comprises a nucleic acid.

66. The method of claim 65 wherein the nucleic acid has a stabilized conformation.

67. The method of claim 48 or 49 further comprising controlling the temperature of the substrate and the ambient temperature and pressure surrounding the reagent-containing droplets and the fluid volumes samples.

68. The method of claim 48 or 52 wherein the biomacromolecule comprises a peptidic biopolymer selected from the group consisting of oligopeptides and polypeptide.

69. The method of claim 68 wherein the biomacromolecule additionally comprises a saccharidic biopolymer selected from the group consisting of oligosaccharides and polysaccharides.

70. The method of claim 48 or 52 wherein the biomacromolecule comprises a nucleotidic biopolymer selected from the group consisting of oligonucleotides and polynucleotides.

71. The method of claim 48 wherein the fluid samples have volume of about 1 picoliter to 30 nanoliters and the reagent-containing droplets have a volume of about 0.1 picoliter to 10 nanoliters.

72. The method of claim 48 wherein at least one of the reagent-containing fluid droplets deposited at the site contains two or more immiscible phases.

73. The method of claim 72 wherein the immiscible phases comprise an aqueous fluid and a phospholipid and the biomacromolecule of interest for crystallization is embedded or anchored in a phospholipid micelle or a phospholipid bilayer.

74. A method for ejecting a different reagent-containing fluid from each of a plurality of fluid reservoirs toward designated sites on a substrate surface to form a combinatorial array of fluid samples on the substrate, containing a biomacromolecule of interest for crystallization, the method comprising the steps of:

(a) positioning an acoustic ejector so as to be in acoustically coupled relationship to a first reservoir containing a first reagent-containing fluid;

(b) activating the ejector to generate acoustic radiation having a focal point near the surface of the first fluid, thereby ejecting a first droplet of the first reagent-containing fluid from the first reservoir toward a first designated site on the substrate surface, whereby the droplet adheres to the designated site;

(c) repositioning the ejector so as to alter the relative positions of the ejector and the first reservoir and to place the ejector in acoustically coupled relationship to a second reservoir containing a second reagent-containing fluid different from the first;

(d) activating the ejector as in step (b) to eject a second droplet of the second reagent-containing fluid from the second reservoir toward the first designated site on the substrate surface, whereby the second droplet adheres to the designated site and mixes with the first droplet;

(e) repeating steps (c) and (d) with additional reservoirs each containing a different reagent-containing fluid until the first designated site on the substrate surface has a fluid sample adhering thereto; and (f) repeating steps (a) through (e) for the remaining designated sites of the array until each site has a fluid sample adhering thereto, wherein each fluid volume sample contains the biomacromolecule of interest for crystallization and each fluid sample occupying a designated site whereby the fluid samples are arrayed on the substrate surface at the designated sites and the composition and chemical conditions at each site are known from the steps of the method and the reagent-containing fluids deposited.

75. The method of claim 74 further comprising repeating steps (a) through (f) to alter the composition of the fluid at each designated site.

76. The method of claim 75 further comprising controlling the physical conditions of the substrate and ambient gas physical conditions surrounding the fluid droplets and the fluid samples.

77. The method of claim 76 wherein the physical conditions controlled are the temperature of the substrate and the ambient gas temperature and pressure.

78. The method of claim 76 further comprising detecting crystallization of the biomacromolecule of interest.

79. The method of claim 78 wherein the detecting step is carried out acoustically.

80. The method of claim 74 wherein at least one of the reagent-containing fluid droplets deposited at the site contains two or more immiscible phases.

81. The method of claim 80 wherein the immiscible phases comprise an aqueous fluid and a phospholipid and the biomacromolecule of interest for crystallization is embedded or anchored in a phospholipid micelle or a phospholipid bilayer.

82. A system for combinatorial experiments to crystallize a moiety of interest and detect crystallization of the moiety of interest, the system comprising:

a plurality of sites arrayed on a substrate;

a plurality of reservoirs each adapted to contain a reagent-containing fluid;

an ejector that is moveable relative to the reservoirs comprising an acoustic radiation generator for generating acoustic radiation and a focusing means for focusing the acoustic radiation at a focal point near the fluid surface in each of the reservoirs; and a means for positioning the ejector in acoustic coupling relationship to each of the reservoirs; and means for detecting crystallization of the moiety of interest; wherein one or more of the materials arrayed on the substrate are contacted with one or more reagent-containing fluids by acoustic ejection, and any physical or chemical change detected at a site upon said contacting denotes a screening result for the material present at said site contacted with said one or more reagent-containing fluids.

83. The system of claim 82 wherein the moiety of interest is a biomacromolecule.

84. The system of claim 82 wherein for said plurality of sites arrayed on the substrate, the sites are present at a density of from about 1,000 to about 100,000,000 sites per square centimeter.

85. The system of claim 82 wherein the means for detecting is acoustic detection.

86. The system of claim 82 further comprising means for ascertaining the quality of the crystals.

87. The system of claim 86 wherein the means for ascertaining the quality of the crystals is by x-ray diffraction or scanning diffractometry.

* * * * *